(12) United States Patent
Walton et al.

(10) Patent No.: US 11,594,306 B2
(45) Date of Patent: Feb. 28, 2023

(54) SYSTEM AND METHOD FOR INCREASING MEDICAL ADHERENCE

(71) Applicant: Express Scripts Strategic Development, Inc., St. Louis, MO (US)

(72) Inventors: Matthew J. Walton, St. Louis, MO (US); Ron D. Strawbridge, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 17/572,355

(22) Filed: Jan. 10, 2022

(65) Prior Publication Data

US 2022/0130498 A1    Apr. 28, 2022

Related U.S. Application Data

(63) Continuation of application No. 15/730,116, filed on Oct. 11, 2017, now Pat. No. 11,222,094.
(Continued)

(51) Int. Cl.
*G16H 10/00* (2018.01)
*G16H 20/10* (2018.01)
(Continued)

(52) U.S. Cl.
CPC .............. *G16H 10/00* (2018.01); *G16H 20/10* (2018.01); *G16H 30/40* (2018.01); *G16H 20/00* (2018.01)

(58) Field of Classification Search
CPC ........ G16H 10/00; G16H 20/10; G16H 30/40; G16H 20/00
See application file for complete search history.

(56) References Cited

U.S. PATENT DOCUMENTS

| 8,666,926 | B1 | 3/2014 | Nease |
| 8,799,016 | B1 | 8/2014 | Cohan |

(Continued)

OTHER PUBLICATIONS

"WaterMinder®—track your daily water intake, hydrate, feel better!", http://waterminderapp.com/, (3 pages).
(Continued)

*Primary Examiner* — Robert A Sorey
*Assistant Examiner* — Kristine K Rapillo
(74) *Attorney, Agent, or Firm* — The Small Patent Law Group

(57) ABSTRACT

A method includes receiving a scheduling request that identifies a medical consumable, accessing first document types that indicate how often medical consumables are to be ingested, identifying a frequency at which the first designated medical consumable is to be consumed based on the first document types, accessing second document types that indicate a pattern of personal activity behavior, identifying one or more temporal opportunity windows based on the second document types, determining one or more matches between the frequency at which the first designated medical consumable is to be consumed and the one or more temporal opportunity windows, creating an adherence schedule based on the one or more matches that indicates when reminders to ingest the first designated medical consumable are to be generated, and generating one or more of the reminders to ingest the first designated medical consumable on a mobile electronic device according to the adherence schedule.

20 Claims, 9 Drawing Sheets

Related U.S. Application Data

(60) Provisional application No. 62/409,821, filed on Oct. 18, 2016.

(51) Int. Cl.
  *G16H 30/40* (2018.01)
  *G16H 20/00* (2018.01)

(56) References Cited

U.S. PATENT DOCUMENTS

| | | | | |
|---|---|---|---|---|
| 8,810,408 | B2* | 8/2014 | Hanson | G16H 40/63 |
| | | | | 128/200.14 |
| 10,124,940 | B2* | 11/2018 | Blackburn | G07F 9/026 |
| 10,438,693 | B1* | 10/2019 | Vandervoort | G16H 10/60 |
| 2014/0316803 | A1 | 10/2014 | Cohan | |
| 2014/0357961 | A1 | 12/2014 | Meltzer | |
| 2015/0006192 | A1 | 1/2015 | Sudharsan | |
| 2015/0100335 | A1* | 4/2015 | Englehard | G16H 40/63 |
| | | | | 705/2 |
| 2015/0100343 | A1* | 4/2015 | Siedlecki | G16H 20/10 |
| | | | | 705/2 |
| 2015/0127380 | A1* | 5/2015 | Aaron | G16H 10/60 |
| | | | | 705/3 |
| 2015/0216413 | A1 | 8/2015 | Soyao | |
| 2015/0265209 | A1 | 9/2015 | Zhang | |
| 2015/0269355 | A1 | 9/2015 | Tidor | |
| 2016/0042306 | A1 | 2/2016 | Emerson | |
| 2016/0140294 | A1 | 5/2016 | Mcbride | |
| 2016/0157735 | A1 | 6/2016 | Zhang | |

OTHER PUBLICATIONS

Holland, Doctor's Orders: Mobile Solutions for Medication Therapy Management,, https://insights.samsung.com/2016/01/21 /doctors-orders-mobile-solutions-for-medication-therapy-management/, Jan. 21, 2016.

* cited by examiner

SYSTEM AND METHOD FOR INCREASING MEDICAL ADHERENCE

CROSS-REFERENCE TO RELATED APPLICATIONS

This application is a continuation of U.S. patent application Ser. No. 15/730,116, filed on Oct. 11, 2017; said application claims the benefit of U.S. Provisional Application No. 62/409,821, filed on Oct. 18, 2016, the entire disclosures of which are incorporated herein by reference.

FIELD

This application relates generally to medical therapy adherence and, more particularly, to improving drug therapy adherence.

BACKGROUND

There is a continuing challenge to reduce the costs of health care. One of the drivers of this cost is prescription drug coverage. Increased prescription drug adherence could lead to reduced waste in medical costs and productivity. Research has shown that non-adherence can have a profound effect on not only an individual's health, but on the health care system as a whole, costing up to $100 billion annually.

Additionally, 33% to 69% of all medication-related hospital admissions in the United States are due to poor medication adherence, and non-adherence contributes to annual indirect costs exceeding $1.5 billion in lost earning and $50 billion in lost productivity. A November 2009 employer survey from the National Pharmaceutical Council found that medication compliance was a top priority for employers, who are looking to their pharmacy benefit managers (PBM) for solutions.

BRIEF SUMMARY

In one embodiment, a method includes receiving (at a computing system) a data scheduling request. The data scheduling request identifies a first designated medical consumable from a pharmacy benefit manager device. The method also includes accessing a plurality of first document types that indicate how often medical consumables that include the first designated medical consumable are to be ingested. The method includes identifying a frequency at which the first designated medical consumable is to be consumed based on at least one of the first document types in the plurality of first document types, and accessing a plurality of second document types that indicate a pattern of personal activity behavior. The method also includes identifying one or more temporal opportunity windows based on the plurality of second document types. The one or more temporal opportunity windows indicate when one or more of the medical consumables are to be ingested. The method includes determining one or more matches between the frequency at which the first designated medical consumable is to be consumed and the one or more temporal opportunity windows, and creating an adherence schedule based on the one or more matches. The adherence schedule indicates when reminders to ingest the first designated medical consumable are to be generated. The method includes generating one or more of the reminders to ingest the first designated medical consumable on a mobile electronic device according to the adherence schedule.

In one embodiment, a tangible and non-transitory computer readable storage medium includes instructions that direct at least one processor to receive (at a computing system) a data scheduling request that identifies a first designated medical consumable from a pharmacy benefit manager device. The instructions also direct the at least one processor to access a plurality of first document types that indicates how often medical consumables that include the first designated medical consumable are to be ingested. The instructions direct the at least one processor to identify a frequency at which the first designated medical consumable is to be consumed based on at least one of the first document types in the plurality of first document types, and to access a plurality of second document types that indicates a pattern of personal activity behavior. The instructions direct the at least one processor to identify one or more temporal opportunity windows based on the plurality of second document types. The one or more temporal opportunity windows indicate when one or more of the medical consumables are ingested. The instructions also direct the at least one processor to determine one or more matches between the frequency at which the first designated medical consumable is to be consumed and the one or more temporal opportunity windows, and to create an adherence schedule based on the one or more matches. The adherence schedule indicates when reminders to ingest the first designated medical consumable are to be generated. The instructions also direct the at least one processor to generate one or more of the reminders to ingest the first designated medical consumable on a mobile electronic device according to the adherence schedule.

In one embodiment, a method includes receiving, at a computing system, a data scheduling request that identifies a first designated medical consumable from a pharmacy benefit manager device. The method also includes accessing a plurality of first document types that indicates how often medical consumables that include the first designated medical consumable are to be ingested, and identifying a frequency at which the first designated medical consumable is to be consumed based on the plurality of first document types. The method also includes monitoring an activity using one or more sensors of a mobile electronic device, and identifying one or more temporal opportunity windows based on the activity that is monitored. The one or more temporal opportunity windows indicate when one or more of the medical consumables are to be ingested. The method includes determining one or more matches between the frequency at which the first designated medical consumable is to be consumed and the one or more temporal opportunity windows, and creating an adherence schedule based on the one or more matches. The adherence schedule indicates when reminders to ingest the first designated medical consumable are to be generated. The method also includes generating one or more of the reminders to ingest the first designated medical consumable on a mobile electronic device according to the adherence schedule.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Figure 1:
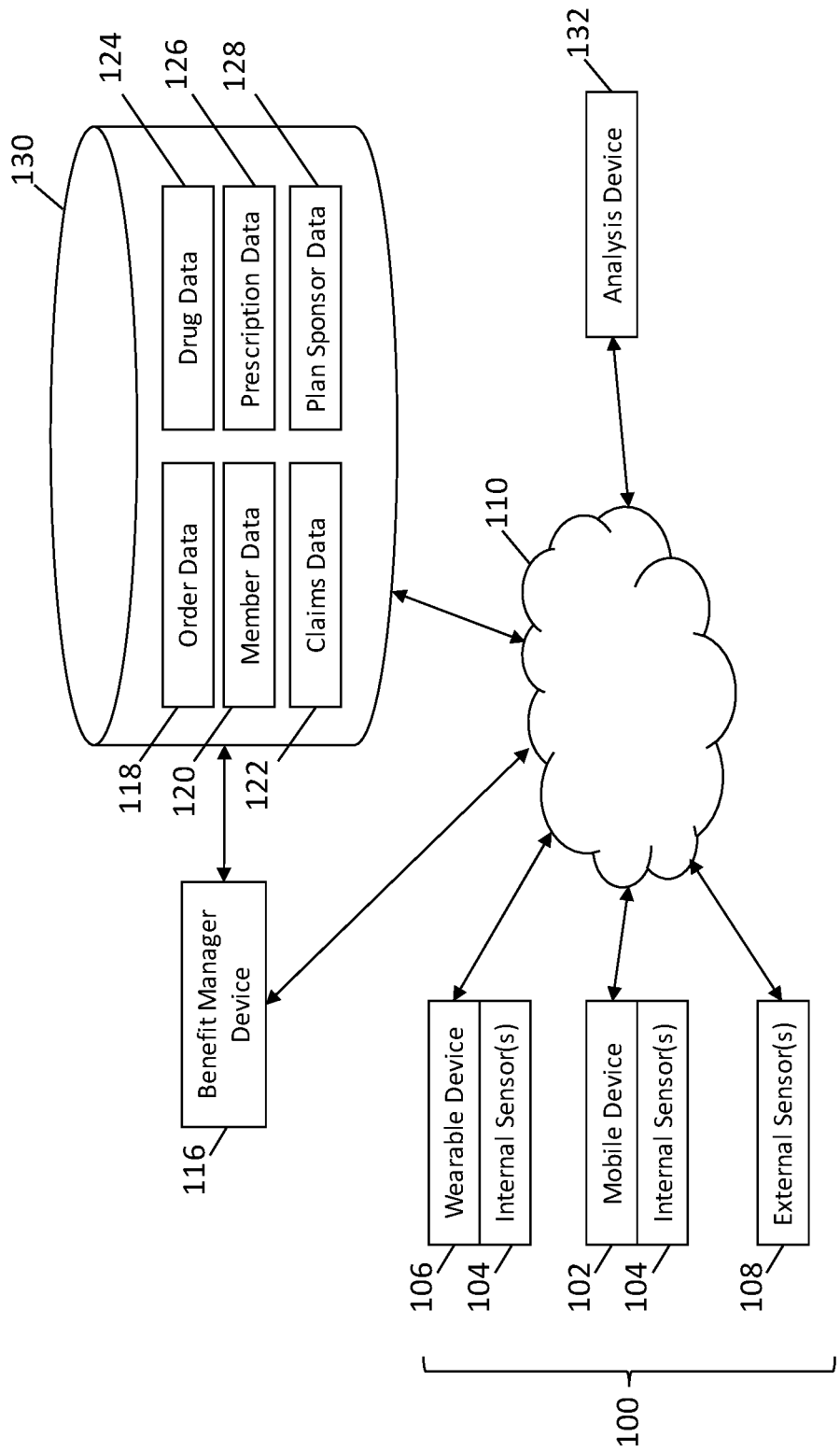
FIG. 1 is a block diagram of a medication reminder system, according to an example embodiment.

Example methods and systems for monitoring and improving therapy adherence are described. In the following description, for purposes of explanation, numerous specific details are set forth in order to provide a thorough understanding of example embodiments. It will be evident, however, to one of ordinary skill in the art that embodiments of the invention may be practiced without these specific details.

The methods and systems are directed to improving adherence to therapy programs; in particular, to adherence to medication therapy and/or to healthcare therapy that includes medication therapy. The methods and systems may also be used to improve compliance with and/or adherence to other wellness and/or health care programs.

In general, the systems and methods described herein may determine therapies and/or schedules for the therapies for mobile device users and may monitor user input and/or sensor data provided by mobile devices to generate intelligent reminders on the mobile devices for the users to increase and/or maintain user adherence to the therapies. The systems and methods may generate the reminders with relatively little or no user input or other configuration by the device user. This generation can avoid user reluctance to provide substantial input for the reminders from being a barrier to generating and providing the reminders. The systems and methods may monitor user adherence to the therapies based on user input, sensor data obtained from sensors in the mobile devices of the users, and/or sensor data obtained from sensors that are external to the mobile devices. Based on the sensor data and, in some embodiments, the user input, the systems and methods can modify the reminders to increase or maintain user adherence. For example, the systems and methods can fine tune the reminders responsive to the sensor data and/or user input indicating that the currently implemented reminders are not increasing or maintaining user adherence to a drug therapy.

A patient (also referred to as a user) may be given a prescription drug as part of a therapy for a particular medical or health condition. In participating in the drug therapy, the patient taking the prescription drug will generally be considered adherent when the patient takes the drug as prescribed. For example, the patient adheres with the therapy when the patient consumes the prescribed medication at the prescribed dosage at the prescribed frequency (e.g., the number of times per day and/or at the appropriate times per day). This may be represented at 100% adherence to the therapy (e.g., the prescribed medications).

The adherence to therapy may be calculated or measured as a medication possession ratio (MPR). The medication possession ratio is a measure that captures a gap in therapy. The medication possession ratio can be used to detect a gap in care over a period of time. Often, measurements of adherence that are based on late refilling of prescriptions are inaccurate because members may be keeping an extra supply on hand to ensure that the members do no run out and appear late to fill. The medication possession ratio is basically a measure that determines if a member has an adequate amount of medication on hand to adequately treat his or her condition.

The medication possession ratio is generally considered as a day supply of medication within a set measurement period divided by the number of days in the measurement period. The medication possession ratio measures the amount of medication someone uses over a reporting period. For example, if there are 100 days in a reporting period and an individual has used 100 pills in this time period, then the ratio may be calculated as 100 pills divided by 100 days, or 100% adherent. If the person only obtained 50 pills in 100 days and the person takes one pill a day, this person is 50% adherent.

If a reporting period starts on May 1st, and a user obtains a prescription for 30 pills filled on April 25th, the calculation of the medication possession ratio may only provide credit for the part of the fill (e.g., the partial fill that started on May 1st). The calculation of the medication possession ratio may only count the number of pills that are actually in the reporting period in order to avoid the error of only counting the fills that actually occurred within the reporting period. Taking an arbitrary window of time measurements for calculating the medication possession ratio, however, may introduce a larger amount of noise. Therefore, the calculation of the medication possession ratio may also evaluate behavior of the patient.

The model may determine when the person fills and measure the medication possession ratio based upon the two points between which they got filled. For example, if the person received a fill on January 1st and the model detects a bunch of fills and the last fill detected for the year is November 30, then the model does not measure that number from January 1st to December 31st, but only measures that number from January 1st to November 30th so that the measurement window is in accordance with the behavior of the number.

The method may utilize an adherence index rather than using a raw score. The adherence index may be determined from a model. The structure of the model may be determined by examining hundreds of variables in historical data and determining patterns. The model may examine data relating to patient demographics such as age and profession and marital status, prescription history such as concurrent drug treatment and length of time on previous treatments, and past behavior such as cessation of other treatments and/or adherence on other medication treatments. Using the patterns certain probabilities can be determined.

In general, the adherence index may be determined by factoring the likelihood or probability of adherence developed from demographic data and other data patterns with the medication possession ratio of the patient. Initially, the model may be built from general population historical demographic data and predicted medication possession ratios. The general population data may also be further segregated by other factors such as by a particular community, or a population within a certain company or a population having a certain category of disease. Individual patient demographics and other individual patient data and individual patient medication possession ratios may be applied against the model to further refine the model. The refinements may be made by evaluating differences between actual and predicted adherence and evaluating related patterns. Once actual data is gathered an actual past medication possession ratio can be factored in to further refine the model.

When the patient does not take the prescribed medication, does not take the prescribed medication at the correct dosage, and/or does not consume the prescribed medication at the prescribed frequency, the patient may generally be deemed to not be adherent or to be less adherent. For example, a patient that consumes the prescribed medication at the prescribed dosage, but at a frequency that is one half of the prescribed frequency may have an adherence of 50% or less. The systems and methods described herein may be used to intelligently generate reminders on mobile devices for patients to consume the prescribed medications in the prescribed manners (e.g., dosages and frequencies), and to fine tune the reminders, so that patient adherence to the prescribed medications can be increased from a current state or can be maintained at a current state.

Different users or patients may be non-adherent to a drug therapy due to a variety of reasons. Some patients may have a positive perceived value of therapy, and are not intentional in their adherence behavior. These patients periodically neglect to take their medications, and, consequently, are not 100% adherent. Other patients may be deemed "active decliners" who do not, for a variety of reasons, place a positive value on the therapy. This could be because the active decliners believe the medication is not effective, are experiencing side effects, do not like being "prescribed for," or do not believe the medication offers sufficient benefit relative to the cost. As a result, these patients actively choose not to take the medications as prescribed. Some patients may be deemed "refill procrastinators" who do a good job taking their medications as long as the patients have the medications on hand. As the medication supply dwindles, however, these patients may delay getting a medication refill. Consequently, these patients may experience a gap in care where they are not taking, and possibly do not have, the prescription drug they are prescribed to take.

The systems and methods of the inventive subject matter described herein may be uniquely applied to pharmaceutical data. For example, the systems and methods may be applied to data generated by or otherwise available to pharmacy benefit managers to determine a plan for a user to adhere to prescriptions and recommended behaviors. Software applications operating on one or more than one mobile device usually carried by patients may obtain some, but not all, of the pharmaceutical data obtained, generated, and/or stored by pharmacy benefit managers. These applications may determine and tailor reminders to individual patients based on the pharmaceutical data obtained from the pharmacy benefit manager(s). In some embodiments, at least a portion of this data is uniquely generated by or otherwise available from pharmacy benefit managers. For example, while different portions of the pharmaceutical data may be separately available from other, disparate sources, the time, expense, and effort to combine and provide this data to the systems and methods described herein may be a substantial barrier to implementation or use by the patients. The pharmaceutical data that is stored by a pharmacy benefit manager can provide a single source of the conglomerated pharmaceutical data for access by the systems and methods. This can substantially reduce the time, effort, and expense needed to determine and modify the reminders to the patients.

The systems and methods described herein may eliminate unnecessary costs and member disruption by customizing adherence reminders for different patients, and by updating or tailoring these reminders as patient behaviors change over time. This can avoid a "one-size-fits-all" reminder solution that may frustrate or annoy some patients, and thereby fail to advance the goal of increasing or maintaining patient adherence. The systems and methods may track patient adherence and communicate with the patients and/or providers to promote proactive action in increasing or maintaining adherence, instead of waiting for adherence to decrease and applying reactive action to the adherence problem.

FIG. 1 is a block diagram of a medication reminder system 100, according to an example embodiment. The system 100 is an example environment in which therapy adherence of patients may be monitored and increased (or at least maintained) by determination, generation, modification, and delivery of reminders to the patients. The system 100 includes a mobile computing device 102 (Mobile Device in FIG. 1) that includes one or more than one sensor 104 (Internal Sensor(s) in FIG. 1).

The mobile device 102 may be a mobile phone, laptop computer, tablet computer, or other handheld computing device having hardware circuitry that includes and/or is connected with one or more than one processor (e.g., one or more than one microprocessor, integrated circuit, and/or field programmable gate array). The mobile device 102 may include an internal memory that stores instructions for directing operations of the mobile device 102 (e.g., one or more than one software application) that are described herein. The mobile device 102 may include one or more than one input device for receiving information and one or more than one output device for presenting information to a user of the mobile device 102. For example, the mobile device 102 can include an electronic display (e.g., touchscreen) that receives user input and visually presents information, a speaker that audibly presents information, or the like.

The internal sensors 104 of the mobile device 102 can include sensors that detect, measure, or otherwise sense characteristics of a user of the mobile device 102 and/or of movement of the mobile device 102. Examples of the internal sensors 104 include accelerometers (e.g., for measuring movement of the user), location determining devices (e.g., global positioning system receivers, wireless triangulation devices, etc.), clocks (e.g., for measuring passage of time, the time of day, the date, etc.), microphones (e.g., for measuring sounds and/or receiving user input), a glucose sensor (e.g., for measuring blood sugars of the user), a blood pressure monitor (e.g., for measuring blood pressures of the user), a pulse oximeter (e.g., for measuring oxygen saturation of the user), a heart rate monitor (e.g., for measuring a pulse of the user), an electrodermal response sensor (e.g., for measuring perspiration of the user), or the like.

The system 100 includes a wearable device 106 (Wearable Device in FIG. 1) that is a mobile computing device that is worn or attached to a user of the mobile device 102. Examples of the wearable device 106 include a smart watch, activity tracking device, etc. The wearable device 106 can include hardware circuitry that includes and/or is connected with one or more processors (e.g., one or more microprocessors, integrated circuits, and/or field programmable gate arrays). The wearable device 106 may include an internal memory that stores instructions for directing operations of the wearable device 106 (e.g., one or more software applications) that are described herein. The wearable device 106 may include one or more than one input device for receiving information and one or more than one output device for presenting information (e.g., medication reminders) to a user of the wearable device 106. For example, the wearable device 106 can include an electronic display (e.g., touchscreen) that receives user input and visually presents information, a speaker that audibly presents information, or the like. The wearable device 106 also may include one or more than one of the internal sensors 104 described above.

The system 100, in some embodiments, includes one or more than one external sensor 108 that detects, measures, or otherwise senses characteristics of a user. Examples of the external sensor 108 include a scale (e.g., for measuring weight or body mass of the user), a glucose sensor (e.g., for measuring blood sugars of the user), a blood pressure monitor (e.g., for measuring blood pressures of the user), a pulse oximeter (e.g., for measuring oxygen saturation of the user), a heart rate monitor (e.g., for measuring a pulse of the user), an electrodermal response sensor (e.g., for measuring perspiration of the user), or the like.

The sensors 104, 108 may directly and/or indirectly communicate with the devices 102, 106 to provide the characteristics measured by the sensors 104, 108 to the devices 102, 106. The sensors 104 may directly communicate with the devices 102, 106 by sending signals representative of the measured characteristics to the devices 102, 106 without the signals being communicated through, over, or via one or more than one communication network 110.

Examples of the network 110 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 110 may include an optical network. The network 110 may be a local area network or a global communication network, such as the Internet. In some embodiments, the network 110 may include a network dedicated to prescription orders.

The sensors 108 may directly communicate with the devices 102, 106 by wirelessly sending signals representative of the measured characteristics to the devices 102, 106 without the signals being communicated through, over, or via one or more than one communication network 110. In some embodiments, one or more than one of the sensors 104, 108 may indirectly communicate with the devices 102, 106 by sending signals representative of the measured characteristics to the devices 102, 106 through, over, or via the communication network 110.

In one embodiment, the system 100 also includes an analysis device 132, which also can be referred to as a back-end analysis device. The device 132 represents a computing system formed from hardware circuitry that includes and/or is coupled with one or more than one processor (e.g., one or more than one microprocessor, field programmable gate array, and/or integrated circuit). As described herein, the analysis device 132 can obtain a portion of the pharmaceutical data from the pharmacy benefit manager device 116 and/or other data sources and, based on this information, create an adherence plan for reminding a user when to take certain medications, when to take certain supplements, when to participate in a therapy, etc. Alternatively, the mobile device 102 may determine the adherence plan.

The analysis device 132 communicates with one or more than one data storage device 130 of a pharmacy benefit manager device 116 to obtain information used to determine what medication reminders to provide to a user of the devices 102, 106 and to customize the reminders for the user. The pharmacy benefit manager device 116 represents a system used by an entity that is at least partially responsible for creation and/or management of the pharmacy or drug benefit. Some or all of the foregoing operations may be performed by executing instructions stored in the benefit manager device 116. The benefit manager device 116 may determine whether to approve or deny claims for pharmacy benefits using a variety of pharmaceutical data stored in a data storage device 130. The data storage device 130 may include a non-transitory storage (e.g., memory, hard disk, CD-ROM, etc.) in communication with the benefit manager device 102 and/or the mobile device 102 directly and/or over the network 110.

The processor(s) of the analysis device 132 may access at least some of the pharmaceutical data stored in the storage device 130 to determine, generate, and customize adherence reminders on the wearable device 106 and/or the mobile device 102. In one embodiment, the analysis device 132 obtains some, but not all, of the data stored in the storage device 130 and used by the pharmacy benefit manager device 116 to adjudicate claims for pharmaceutical benefits. The pharmacy benefit manager device 116 may have a conglomerate of pharmaceutical data at a single source (e.g., the pharmacy benefit manager device 116) that is not otherwise available to the mobile device 102.

In one embodiment, the analysis device 132 may use sensor data and pharmaceutical data to assist the user in obtaining prescribed medications. For example, responsive to a notification being generated on the wearable device 106 to remind the user to obtain a refill of a prescribed medication, the mobile device 102 may use the location of the user (e.g., as determined by a global positioning system receiver of the sensors 104, 108) and a database of current prices for the medication (e.g., which may be obtained via the network 110) to determine the lowest price (or a lower price) for the medication near the location of the user.

The pharmaceutical data that is in the possession of the pharmacy benefit manager device 116 can include order data 118, member data 120, claims data 122, drug data 124, prescription data 126, and/or plan sponsor data 128 stored in the data storage device 130. The order data 118 may be related to a prescription order. The order data 118 may include type of the prescription drug (e.g., drug name and strength, etc.) and quantity of the prescription drug, etc. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like.

The order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription bottle and sealing lid, prescription packaging and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets, bins, trays, carts, and the like used to transport prescriptions within the pharmacy may also be stored as order data 118. In some embodiments, a portion of the order data 118 may be provided in adherence reminders. For example, an image of a pill to be taken that was captured during as order data 118 may be visually presented on the mobile device 102 and/or the wearable device 106 as part of an adherence reminder.

The member data 120 includes information regarding the members associated with the pharmacy benefit manager device 116. The information stored as member data 120 may include personal information, personal health information, protected health information, and the like. Examples of the member data 120 include name, address, telephone number, e-mail address, prescription drug history, etc., and the like. The member data 120 may include a plan sponsor identifier that identifies the plan sponsor associated with the member and/or a member identifier that identifies the member to the plan sponsor. The member data 120 may include a member identifier that identifies the plan sponsor associated with the patient and/or a patient identifier that identifies the patient to the plan sponsor. The member data 120 may also include, by way of example, dispensation preferences such as type of label, type of cap, message preferences, language preferences, or the like.

In some embodiments, the member data 120 may include information for persons who are patients of the pharmacy but are not members in the pharmacy benefit plan being provided by the pharmacy benefit manager device 116. For example, these patients may obtain drug directly from the pharmacy, through a private label service offered by the pharmacy, a fulfillment center, or otherwise. In general, the use of the terms member and patient may be used interchangeably herein.

The claims data 122 includes information regarding pharmacy claims adjudicated by the pharmacy benefit manager device 116 under a drug benefit program provided by the pharmacy benefit manager device 116 for one, or more than one, plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier number, medication class, the cost of the prescription drug provided under the drug benefit program, the copay/coinsurance amount, rebate information, and/or member eligibility, etc. Additional information may be included.

In some embodiments, other types of claims beyond prescription drug claims may be stored in the claims data 122. For example, medical claims, dental claims, wellness claims, or other type of health care-related claims for members may be stored as a portion of the claims data 122.

In some embodiments, the claims data 122 includes claims that identify the members with whom the claims are associated. In some embodiments, the claims data 122 includes claims that have been de-identified (e.g., associated with a unique identifier but not with a particular, identifiable member, etc.).

The drug data 124 may include drug name (e.g., technical name and/or common name, etc.), other names by which the drug is known by, active ingredients, an image of the drug (e.g., in pill form, etc.), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the pharmacy benefit manager device 116. Examples of the plan sponsor data 128 include company name, company address, contact name, contact telephone number, contact e-mail address, etc., and the like.

The processor(s) of the analysis device 132 may only be able to obtain some of this pharmaceutical data in order to determine, generate, and customize therapy reminders delivered to a user via the wearable device 106 and/or the mobile device 102. For example, the pharmacy benefit manager device 116 may only allow the analysis device 132 to download or otherwise access (e.g., via the network 110) the portions of the order data 118, the drug data 124, and/or the prescription data 126 related to the user (and not for other users). The analysis device 132 can access these portions of the pharmaceutical data in order to determine the types and/or quantities of prescription drugs prescribed to the user, the information in the prescription materials instructing how the drugs are to be consumed (e.g., the frequency at which the drugs are to be consumed), interaction warnings, side effects, expiration dates, prescription date, drug names, active ingredients, the prescriptions issued by prescribers on behalf of the user, dosing information, and the like.

In one embodiment, the pharmacy benefit manager device 116 may not allow the analysis device 132 to download or otherwise access (e.g., via the network 110) the member data 120 or the plan sponsor data 128. In some embodiments, the pharmacy benefit manager device 116 may allow the analysis device 132 to download or access the portion of the member data 120 and/or the plan sponsor data 128 relating to the user, but not other member data 120.

The pharmacy benefit manager device 116 may allow the analysis device 132 to download or otherwise access (e.g., via the network 110) only a portion of the claims data 122, such as the prescription drugs that were filled by the pharmacy (e.g., the national drug code numbers) and/or the dispensing dates, but not the remainder of the claims data 122.

The portions of the pharmaceutical data that are obtained by the mobile device 102 may not be otherwise available to the analysis device 132 without significant user intervention. For example, a user may otherwise be required to individually enter the names of prescribed medications, the prescribed dosages of the medications, the prescribed frequencies at which the medications are to be consumed, etc.

To avoid requiring this significant user intervention, the user may provide login information (e.g., a unique login name, password, or a unique combination of a login name and password) to the mobile device 102 via a user interface displayed by the mobile device 102 on the mobile device 102 or the wearable device 106. The processor(s) of the mobile device 102 provide this information to the analysis device 132, which can then request pharmaceutical data from the pharmacy benefit manager device 116. The pharmacy benefit manager device 116 may then allow the processor(s) of the analysis device 132 to access (e.g., download or otherwise acquire) the portions of the pharmaceutical data associated with the user. The processor(s) of the analysis device 132 access this data to determine which medications are prescribed to the user, the dosing information for those medications (e.g., the amount and/or frequency of consumption), and drug interactions for those medications.

Figure 2:
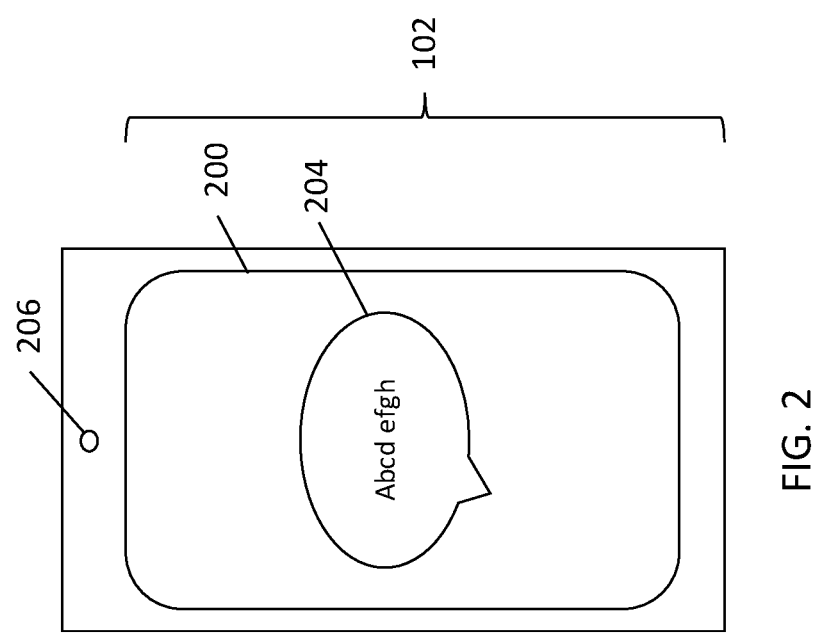
FIG. 2 illustrates one example of a mobile device.
Figure 3:
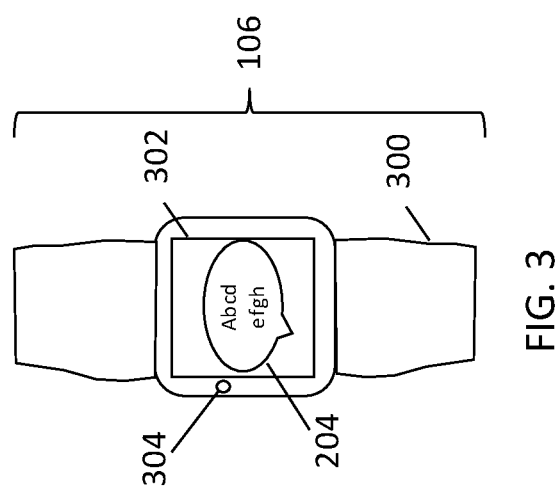
FIG. 3 illustrates one example of a wearable device.

FIG. 2 illustrates one example of the mobile device 102 and FIG. 3 illustrates one example of the wearable device 106. The mobile device 102 is shown as a mobile phone, but, in some embodiments, may be another type of handheld device, such as a tablet computer, laptop computer, etc. The mobile device 102 includes one or more than one input/output device 200, such as a touchscreen. In some embodiments, the mobile device 102 can include an input device (e.g., a keyboard) and an output device (e.g., an electronic display). The input/output device 200 presents information to the user of the system 100 and, in some embodiments, receives input from the user. The information may be provided in the form of a notification 204, such as an electronically presented visual display that informs the user, such as through text, images, icons, etc., that remind the user when to take a medication, which medication to consume, how much of the medication to consume, which medications or foods to avoid consuming, etc. In some embodiments, the notification 204 may request a response from the user, such as by asking the user how he or she is feeling. This response may be used to customize or tailor future notifications 204 to the user, as described below.

In some embodiments, the mobile device 102 can include a camera 206 as an additional input device. As described below, the camera 206 can be used to capture images of medication taken by the user to generate pharmaceutical data useful for generating, providing, and/or customizing reminders or notifications 204 for the user.

The wearable device 106 is represented in FIG. 3 as a watch, but, in some embodiments, may be another type of device that is worn or otherwise attached to or otherwise proximate to the user. The wearable device 106 includes one or more than one input/output device 302, such as a touchscreen, and a coupling apparatus 300, such as a band, that secures the wearable device 106 to the user. In one embodiment, the coupling apparatus 300 may include or be connected with one or more sensors 104, such as a glucose sensor, an electrocardiogram sensor, etc. The input/output device 302 presents information to the user of the system 100 and, in some embodiments, receives input from the user. The information may be provided in the form of the notification 204 described above.

In some embodiments, the wearable device 106 can include a camera 304 as an additional input device. As described below, the camera 304 can be used to capture images of medication taken by the user to generate pharmaceutical data useful for generating, providing, and/or customizing reminders or notifications 204 for the user.

Although not visible in FIG. 2 or 3, the devices 102, 106 may include one or more than one sensor 104 described above and communication circuitry, such as antennas and transceiving circuitry, for allowing communication (e.g., wireless communication) between the devices 102, 106 and/or between the devices 102, 106 and other components described herein via the network 110. In some embodiments, the mobile device 102 may be a smart phone, personal digital assistant, tablet computer, or laptop computer, and the wearable device 106 may be a smart watch or activity tracking device.

Figure 4:
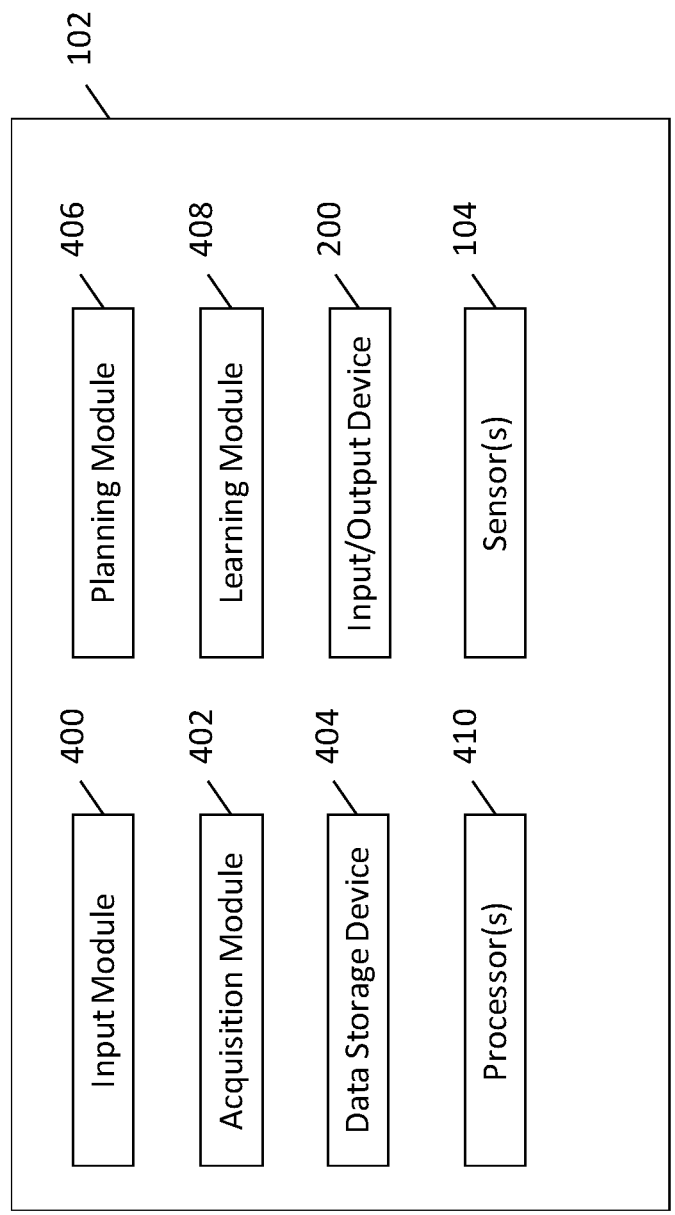
FIG. 4 is a block diagram of one example of the mobile device.

FIG. 4 is a block diagram of one example of the analysis device 132. The analysis device 132 includes several modules, which can be deployed in a memory or data storage device 404 of the analysis device 132 and executed by the one or more than one processor 410. An input module 400 receives data from the pharmacy benefit manager device 116 (e.g., portions of pharmaceutical data for users, as described above), input from a user of the mobile device 102, and/or data from the sensors 104, 108. The input provided from the user can include login credentials or other identifying information that may be used by the analysis device 132 to obtain the pharmaceutical data associated with the user.

The analysis device 132 receives a data scheduling request that identifies one or more designated medical consumables. These consumables may be identified from information provided by or accessed via the pharmacy benefit manager device 116. The consumables can be prescribed medications, over-the-counter medications, foods, or the like. An acquisition module 402 obtains at least some pharmaceutical data from the pharmacy benefit manager device 116 responsive to receiving the request. The acquisition module 402 can provide the login credentials of the user to the pharmacy benefit manager device 116. If the pharmacy benefit manager device 116 approves the user for receiving the pharmaceutical data (e.g., the login credentials match an approved login credential combination), then the pharmacy benefit manager device 116 can communicate the portion of the pharmaceutical data that is relevant to the user to the acquisition module 402.

In one embodiment, the pharmacy benefit manager device 116 may have a database, list, or other memory structure of members of one or more insurance plans managed by the pharmacy benefit manager device 116 (e.g., in the member data 120). If the login credentials obtained by the input module 400 match information for a member of a plan managed by the pharmacy benefit manager device 116, then the pharmacy benefit manager device 116 can determine that the user is a member and can provide the portion of the pharmaceutical data that is relevant to the user and that is used by the system 100 to generate, provide, and customize the reminders to the acquisition module 402 (e.g., via the network 110). This ensures that the acquisition module 402 obtains the pharmaceutical data indicative of which prescribed medications that the user is currently taking (or currently prescribed but not taking), dosing information for these medications, interaction warnings, etc.

The acquisition module 402 in some embodiments may instruct the mobile device 102 and/or the wearable device 106 to generate a notification 204 requesting that the user provide additional medication information or confirm that no additional medication information is to be provided. For example, if the user is not a member of a plan managed by the pharmacy benefit manager device 116 or is a member, but is taking additional medications that are not in the records of the pharmacy benefit manager device 116, then the mobile device 102 and/or wearable device 106 can, under the direction of the analysis device 132, provide the user with the ability to provide the pharmaceutical data needed to generate, provide, and customize the notifications 204. This may occur by the acquisition module 402 instructing the user to take a picture of a medication container (e.g., pill bottle, exterior box of medication, etc.) using the camera 206 and/or 304. In some embodiments, the user may provide pharmaceutical data associated with the cash purchase of prescription drugs that are not otherwise adjudicated by, or known to, the pharmacy benefit manager device 116.

The acquisition module 402 may perform optical character recognition on images obtained by the camera 206, 304 to determine which medication is shown in an image, the dosing information printed on a container of the mediation, etc., as the pharmaceutical data used by the system 100. In some embodiments, the images may be compared against images taken of the prescription drug prior to dispensing in a pharmacy (e.g., a mail order pharmacy or retail pharmacy in which the medication was dispensed). This process can automatically add substantial pharmaceutical data to the analysis device 132 without requiring the user to manually type in or select the medications, dosing information, etc.

In some embodiments, the acquisition module 402 may receive the pharmaceutical data from the user by the user typing or selecting the medications, dosing information, etc. In one embodiment, the acquisition module 402 obtains the medications, dosing information, etc., from a combination of sources. For example, information on prescribed medications may be obtained from the pharmacy benefit manager device 116 and/or the images taken by the camera 206, 304, and information on over-the-counter medications or supplements (e.g., medications or supplements that are not prescribed by a healthcare provider) can be obtained from the images taken by the camera 206, 304.

The acquisition module 402 can store the pharmaceutical data received from the pharmacy benefit manager device 116 and/or the user in one or more than one data storage device 404, such as a non-transitory storage (e.g., memory, hard disk, CD-ROM, etc.). In one embodiment, the acquisition module 402 obtains a plurality of document types from the manager device 116 as the pharmaceutical data. These document types can be data structures that indicate how often various medical consumables are to be ingested or otherwise consumed. For example, the document types can indicate, for example, that penicillin is to be ingested with water twice a day, that an over-the-counter medication is to be ingested only once a day, and so forth.

A planning module 406 creates a preliminary or initial adherence schedule or plan for generating notifications 204 to remind the user when and/or how to take the medications. The adherence plans described herein may designate what notifications 204 are to be provided (e.g., what information is to be presented on the output device 200 and/or 302 in text and/or images) and when the notifications 204 are to be provided (e.g., dates, times, locations, etc.). The preliminary or initial adherence plan may be based on data provided by extendable internal data sources.

The extendable internal data sources can include the pharmacy benefit manager device 116 providing the portions of the claims data 122, prescription data 126, order data 118, and details of the medications relevant to the user. The data sources can include the user providing images and/or information on supplements taken by the user, over-the-counter medications, or prescriptions provided or obtained by another pharmacy benefit manager. The data sources can include data provided by the external sensors 108. In some embodiments, other data sources can be used. In one embodiment, one or more than one additional data source may be added to the group of extendable internal data sources as time progresses. For example, the pharmacy benefit manager device 116 may add another type of pharmaceutical data that may be useful in determining when to remind patients of a certain demographic group on how or when to take certain medications.

The preliminary or initial adherence plan can be created based on the data from the extendable internal data sources. The pharmaceutical data may provide prescribed or recommended dosages and consumption frequencies of the prescribed medications. The prescription data 126 may include another plurality of document types (e.g., data structures) that identify frequencies at which various designated medical consumables are to be consumed. For example, these document types can indicate that a first amount of an antibiotic medication is to be taken three times a day for ten days (as indicated by a first prescription), a different, second amount of a statin medication is to taken once a day for an unidentified duration (as indicated by a different, second prescription), a test strip is to be used at least six times a day to test the blood glucose level of the user for an unidentified duration (as indicated by a different, third prescription), insulin is to be consumed in an amount between forty and sixty milliliters per day for an unidentified duration (as indicated by a different, fourth prescription), and a different, third amount of chlorthalidone to be consumed once per day. The additional data provided by the user (e.g., an image of a multivitamin bottle) may indicate that the user is to consume one multivitamin pill per day for an unidentified duration.

The planning module 406 can examine the data provided from the extendable internal data sources to determine the preliminary or initial adherence schedule. This schedule or plan may dictate the dates, times, and/or types of reminders 204 that are to be provided to the user on the wearable device 106 (and/or the mobile device 102) to remind the user when to take certain medications. The types of reminders 204 may designate the verbiage and/or images to be shown for a reminder 204, and/or whether the reminder is to be provided audibly, visually, and/or haptically (e.g., by vibrating the wearable device 106 and/or mobile device 102). The planning module 406 can create the preliminary adherence plan using the data provided from the extendable internal data sources and the data provided from the extendable device data sources to cause the times, dates, and/or types of reminders 204 to avoid conflicting with the behavioral data.

Figure 5:
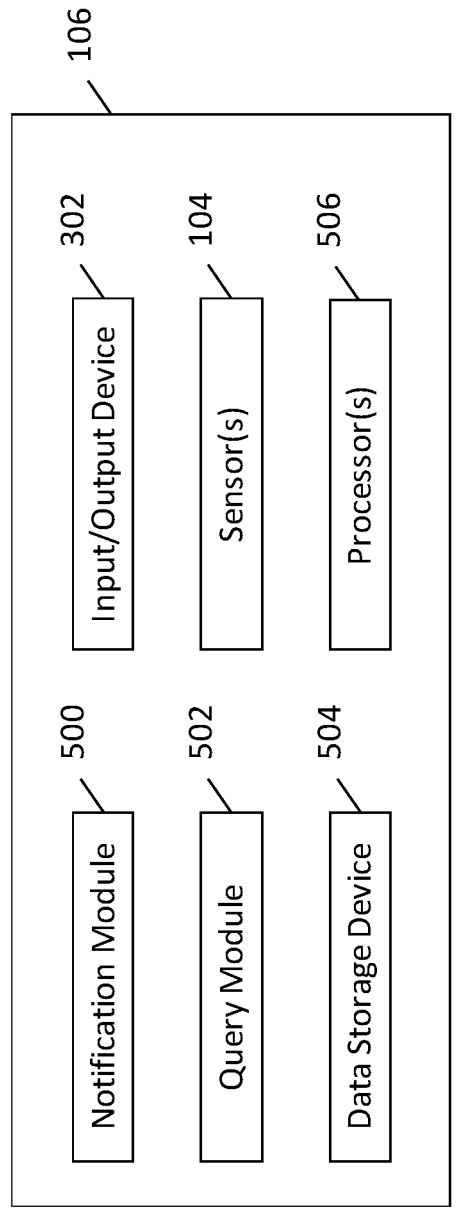
FIG. 5 is a block diagram of one example of the wearable device.

With continued reference to the analysis device 132 shown in FIG. 4, FIG. 5 is a block diagram of one example of the device 106. The device 106 optionally can represent the mobile device 102. The device 106 includes several modules, which can be deployed in a memory or data storage device 504 of the device 106 and executed by the one or more than one processor 506. A notification module 500 receives input from the analysis device 132 (e.g., a signal communicated through the network 110) to determine which notifications 204 to present on the input/output device 302.

Responsive to receiving instructions from the analysis device 132 (e.g., the planning and/or learning modules 406, 408) that describe an adherence plan, the notification module 500 can generate and communicate signals to the input/output device 302 to direct the input/output device 302 to provide the notifications 204 at the times and in the manner dictated by the adherence plan. The details of an adherence plan may be stored in the memory 504 of the device 106.

A sensor 104 of the device 106 can represent the camera 206 or the camera 304. The sensor 104 may obtain images or video of medication or supplement containers, written prescription instructions, or the like, which can be received by a query module 502 and communicated to the acquisition module 402 of the analysis device 132 for determining the prescription data (as described above).

Returning to the description of the analysis device 132, and continuing with the example described above, the planning module 406 could create the preliminary or initial adherence plan that directs first notifications 204 to be provided at 8:00 am, 4:00 pm, and 12:00 am to remind the user to consume the antibiotic medication, second notifications 204 to be provided at 12:00 am to remind the user to consume the statin medication, third notifications 204 to be provided at 4:00 am, 8:00 am, 12:00 pm, 4:00 pm, 8:00 pm, and 12:00 am to remind the user to use the test strips to test the blood glucose level of the user, a fourth notification 204 to be provided at 12:00 pm to remind the user to consume between forty and sixty milliliters of the insulin, a fifth notification 204 to be provided at 12:00 pm to remind the user to consume chlorthalidone (e.g., to lower or keep the blood pressure of the user below a designated pressure), and a sixth notification 204 to be provided at 12:00 am to remind the user to consume the multivitamin.

Optionally, the planning module 406 can create the plan or schedule based not on time (or, in addition to being based on time), but based on location. With respect to locations, the device 106 can monitor changing geographic locations of the patient while the patient is moving (e.g., between work and home, or between other locations). The planning module 406 can determine when the patient is within a designated area (e.g., a geofenced area) and cause a reminder or notification to be provided when the patient is within this area (or prevent the reminder or notification from being provided while the patient is outside of this area). This can ensure that the patient is reminded to consume a medication when the patient returns home, arrives at work, or the like.

The preliminary or initial adherence plan may conflict with behavior of the user, as indicated by data provided by extendable device data sources. The extendable device data sources include the sensors 104, 108 and/or cameras 206, 304. The data provided by these sensors 104, 108 can include a variety of characteristics about the user, such as locations of the user (e.g., as determined by a global positioning system receiver or other sensor), caloric intake of the user (e.g., as determined by images taken of food packaging by the cameras 206, 304), movements of the user (e.g., as determined by accelerometers in the device 102 and/or device 106), sleep patterns or durations (e.g., as determined based on the movements of the user), activity levels of the user (e.g., as determined based on the movements of the user), blood glucose measurements (e.g., as determined by a blood sugar machine), blood pressure measurements (e.g., as determined by a blood pressure sensor), or the like.

The extendable device data sources may provide data that provides further guidance on when reminders to consume the medications or supplements should be provided by the user. Behavioral data provided by the extendable device data sources indicates or represents how the user behaves on a regular basis. The behavioral data can include or be based on the data provided by the sensors 104 of the mobile device 102, by the sensors 104 of the wearable device 106, and/or the external sensors 108. At least some of this data may be stored in the memory of the wearable device 106 and/or mobile device 102, and/or communicated to the analysis device 132 from the wearable device 106 and/or the mobile device 102. This information can be stored as another plurality of document types that indicates a pattern of personal activity behavior of a patient.

One example of the behavioral data can include the latest time or times at which movements are measured by one or more than one accelerometer in the mobile device 102 and/or wearable device 106 and/or the earliest time or times that these movements are measured. The latest time or times can indicate when the user typically goes to sleep, and the earliest time or times can indicate when the user is waking up. More intense movements (e.g., greater accelerations) may indicate times that the user is exercising, potentially on a regular basis. Blood glucose measurements can indicate when the blood glucose levels of the user tend to be high or lower than designated thresholds (e.g., greater than 150 milligrams per deciliter or less than seventy milligrams per deciliter). Location measurements can indicate when the user is at home, at work, at a gym, etc. Movements measured during sleep of the user (or an absence thereof) can indicate time periods of restfulness or deep sleep. Blood pressure measurements can indicate time periods when the blood pressure of the user is elevated or low (e.g., above 120/80 milligrams of Hg or below 90/60 milligrams of Hg). Measurements of the weight of the user can indicate weight gains or losses. This or other behavioral data provided by the extendable device data sources can be measured by the wearable device 106 and/or mobile device 102, which users tend to wear or carry with them on a regular and continual basis. This allows the behavioral data to be monitored and changes in the behavioral data tracked to update the adherence plan as time progresses, as described below.

A learning module 408 of the analysis device 132 examines the behavioral data to identify temporal gaps in the schedules of the user. A temporal gap is a time period in which the behavior data indicates that the user is not normally or otherwise preoccupied with sleep, exercise, etc. A temporal gap also can be referred to as a temporal opportunity window. These gaps or windows can be periods of time where the patient is inactive, such as not moving in a vehicle, not exercising, or the like. As one example, if the behavioral data indicates that the user typically is asleep from 10:00 pm until 6:00 am, then the learning module 408 may modify the preliminary or initial adherence plan to a plan that does not provide notifications 204 outside of the window from 6:00 am to 10:00 pm (unless a prescription for the user requires consumption of a medication during this time period). Moreover, the learning module 408 may determine which medications require more frequent consumption (e.g., the blood glucose tests) and direct that the reminders 204 for those medications be provided at times that the user typically wakes up and before the user goes to sleep. The learning module 408 may avoid directing reminders 204 be given when the user is typically exercising or away from home, and may schedule reminders 204 to be provided when the user arrives home.

In one embodiment, the learning module 408 determines one or more matches between the frequencies at which designated medical consumables are to be consumed and the temporal opportunity windows that are identified. If there are sufficient opportunity windows during a day to consume a medication as the designated frequency, then the learning module 408 identifies a match between the frequency of the consumable and the opportunity windows of the patient.

The planning module 406 and/or the learning module 408 may create or modify the adherence plan to implement "if/then" logic. For example, a prescription may require that a medication be administered only after the user is upright for at least fifteen minutes. The planning module 406 may create the adherence plan or the learning module 408 may change the adherence plan to provide a reminder 204 to the user to be upright (e.g., standing) at a designated time, and then monitor movements detected by the sensors 104. If the user remains upright for at least this period of time, then the adherence plan may direct the wearable device 106 to provide a notification 204 to remind the user to consume the medication.

Figure 6:
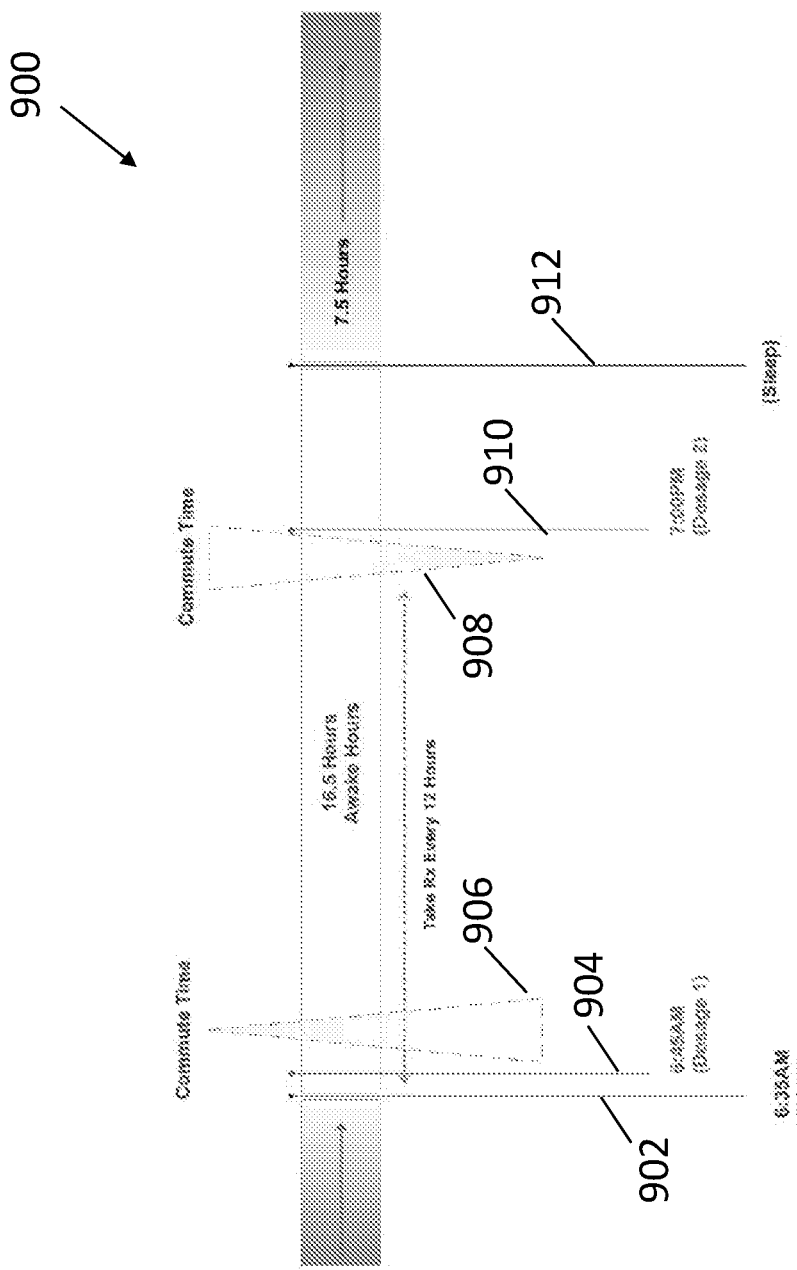
FIG. 6 illustrates one example of a timeline that represents generation or modification of an adherence plan by a planning module and/or a learning module shown in FIG. 4.

FIG. 6 illustrates one example of a timeline 900 that represents generation or modification of an adherence plan by the planning module 406 and/or the learning module 408. The timeline 900 represents one day in the adherence plan. As shown, the patient wakes up at a first time 902 along the timeline 900 (e.g., 6:35 a.m.). The learning module 408 can determine this first time 902 based on when one or more of the sensors 104, 106 detect movement of the patient after a prolonged period of time of less movement, or little to no movement (e.g., during sleep). The adherence plan is created to that a first daily reminder for the patient to take a dosage of medication does not occur until a second time 904, which occurs after the patient wakes up (e.g., at the first time 902). Optionally, the learning module 408 can determine from sensor data that the patient is commuting during a first time period 906. The learning module 408 can modify the adherence plan to ensure that the first daily reminder is provided at the time 904 that is after the patient wakes up (the first time 902) and before the patient begins his or her commute (during the time period 906).

The planning module 406 can determine that the medication is to be taken once every twelve hours based on user input and/or the prescription data. This may result in the adherence plan being created with a reminder to take the second dosage of the medication twelve hours after the first time 902, or at 6:35 p.m. But, data from the sensors 104, 106 (e.g., detection of movement from a global positioning system receiver) can indicate that the patient is driving or otherwise traveling during a second time period 908 that extends over the time that is twelve hours after the first dosage. The learning module 408 may therefore change the time at which the reminder is provided. Because the patient is moving during the initial planned reminder time and the prescription data prohibits taking the medication before the time period in which the patient is driving or otherwise traveling, the learning module 408 can modify the adherence plan to provide the reminder for the second dosage at a later time 910. The time 910 at which this second reminder is provided can be set by the learning module 408 to occur before the patient goes to sleep at a later time 912, as determined based on sensor data.

The planning module 406 and/or the learning module 408 may schedule the reminders to avoid notifications 204 being provided that would contradict or violate drug interaction warnings from the order data 118. For example, if a first medication should not be taken within six hours of a second medication due to an interaction warning, then the planning module 406 may create the adherence plan and/or the learning module 408 may modify the adherence plan to avoid notifications 204 being provided that would cause the user to consume the first and second medications within this time window or period.

Figure 7:
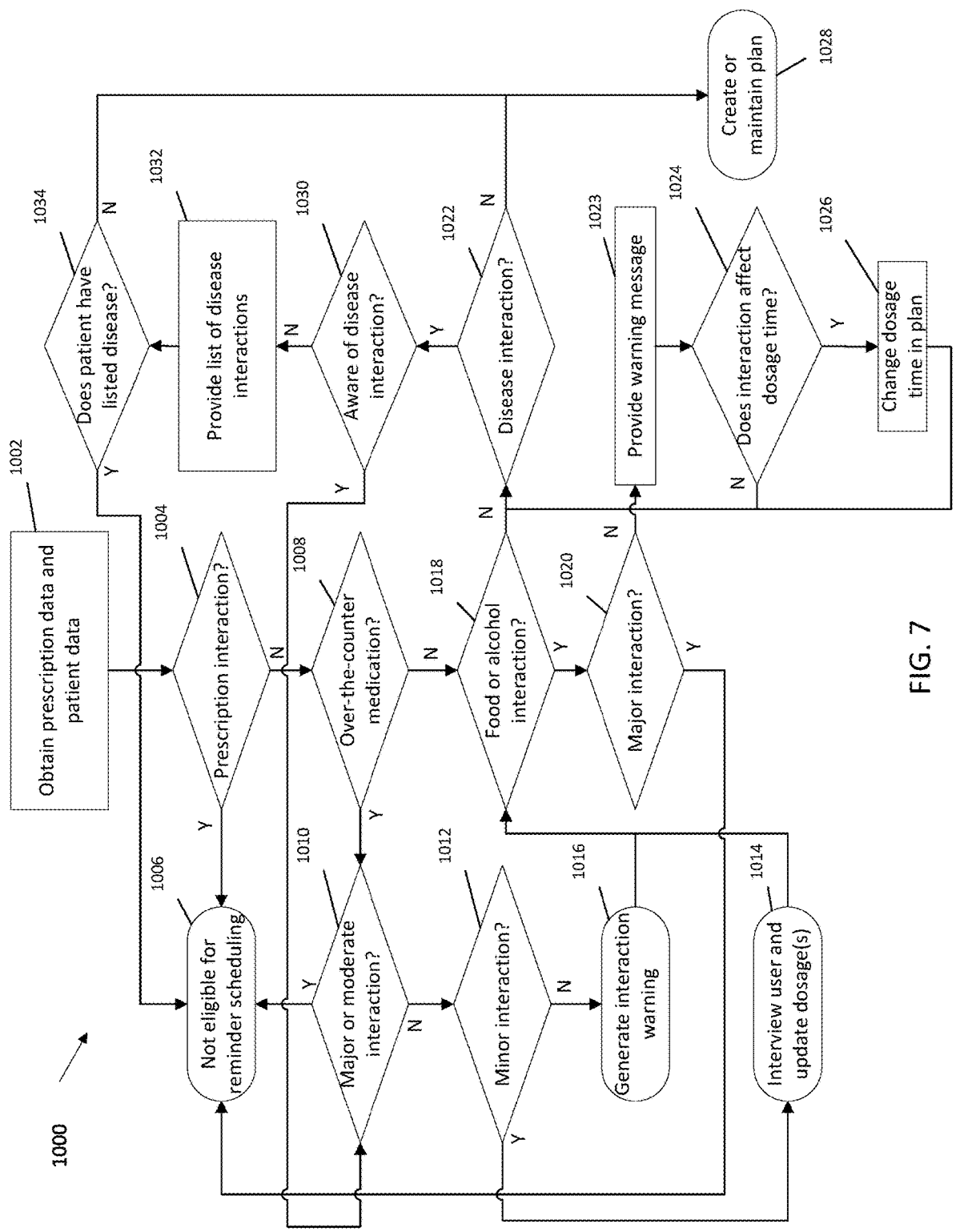
FIG. 7 illustrates a flowchart of one embodiment of a method for scheduling reminders to avoid drug interactions.

FIG. 7 illustrates a flowchart of one embodiment of a method 1000 for scheduling reminders to avoid drug interactions. The method 1000 can represent operations performed by the planning module 406 and/or learning module 408 to avoid generating or modifying a plan that would result in the plan generating reminders to consume one or more medications that negatively or dangerously interact with each other.

At 1002, prescription data 126 and patient data (e.g., member data 120) are obtained. An initial plan may already be created or may be created by the planning module 406 using this prescription data and patient data. At 1004, a determination is made as to whether there is an interaction between two or more prescriptions. The planning module 406 and/or learning module 408 may refer to a table, list, or other memory structure in the data storage device 404 that stores various combinations of prescriptions having negative interactions. These interactions can cause various negative consequences on the patient, such as an increased risk of death, allergic reactions, unintended increases in the impact of certain medications, nullification of certain medications, decreased reaction times, insomnia, nausea, other increases in discomfort to the patient, etc. The module 406 and/or 408 can compare the medications prescribed to the same patient to the stored interactions and determine if any combination of two or more prescribed medications match the stored interactions. If an interaction between prescribed medications is identified, then flow of the method 1000 can proceed toward 1006. Otherwise, if no interaction is identified, then flow of the method 1000 can proceed toward 1008.

At 1006, a determination or decision is made that the prescribed medications cannot be used in the plan provided to the patient. Because at least one combination of prescribed medications results in a drug interaction, the modules 406 and/or 408 do not create or modify the plan to schedule reminders to take the interacting medications. Flow of the method 1000 may then terminate or can return toward 1002 in the event that the prescribed medications have changed to avoid the interaction.

At 1008, with no drug interaction being discovered, a determination is made as to whether the patient is consuming one or more than one over-the-counter medication. The over-the-counter medication can be a supplement, drug, or the like, that is not prescribed by a medical professional or that does not require a prescription for a patient to acquire the medication. The planning and/or learning modules 406, 408 can query the patient by directing the input/output device 200 and/or 302 to ask the patient if the patient is consuming (or is planning on consuming) any over-the-counter medications. The patient can provide input into the input/output device 200, 302 that indicates whether the patient is consuming or planning on consuming one or more over-the-counter medications. Optionally, another source can provide the input indicating the over-the-counter medication, such as scanning a bar code, quick response code, image, or the like, on a container of the over-the-counter medication to indicate that the patient is consuming or planning on consuming the over-the-counter medication.

If the input indicates that the patient is consuming or planning on consuming the over-the-counter medication, then flow of the method 1000 can proceed toward 1010. If the input does not indicate that the patient is consuming or planning on consuming the over-the-counter medication, then flow of the method 1000 can proceed toward 1018.

At 1010, a determination is made as to whether there is a major or moderate interaction between the over-the-counter medication(s) and the prescribed medications. The analysis device 132, mobile device 102, and/or wearable device 106 can store different set of interactions between prescribed medications, between any prescribed and over-the-counter medications, between any prescribed medication and foods, between any prescribed medication and alcohol (and/or other drugs), between any prescribed medication and other consumables, and/or between any prescribed medication and a disease of the patient. These interactions can be stored in the storage devices 404, 504, or in another location, and can be categorized based on the severity of the side effects of the interactions. Interactions having more severe effects can be included in a major interaction category, interactions having lesser effects can be included a moderate interaction category, interactions having even lesser effects can be included in a minor interaction category, and so on. The planning and/or learning module 406, 408 can determine whether there is an interaction between the prescription medication and over-the-counter medication and which category the interaction falls into, and classify the interaction accordingly. If there is an interaction and the interaction is classified as a major or moderate interaction, then flow of the method 1000 can proceed toward 1006, where the plan is not created or is created without including reminders to consume the prescribed medication and/or the over-the-counter medication. If there is no interaction or the interaction is not classified as a major or moderate interaction, then flow of the method 1000 can proceed toward 1012.

At 1012, a determination is made as to whether there is a minor interaction between the prescribed medication and the over-the-counter medication. If there is such an interaction, then flow of the method 1000 can proceed toward 1014. If there is no such interaction, then flow of the method 1000 can proceed toward 1016.

At 1014, the patient (also referred to as a user) is interviewed and dosages of the over-the-counter medication can be updated. For example, the planning and/or learning module 406, 408 can ask the patient a series of questions via the input/output devices 200, 302 that determine how often, how much, and when the over-the-counter medication is being consumed. The answers to these interview questions from the patient can be compared to pre-stored rules or criteria that determine whether the dosage(s) and/or times of the over-the-counter medication can interact with the prescribed medication(s). This comparison can allow the planning and/or learning modules 406, 408 to determine whether the dosage(s) and/or times at which the over-the-counter medication is consumed can be modified to eliminate or reduce the severity of the interaction. The plan can then be created and/or modified with the changed dosages of the over-the-counter medication. Flow of the method 1000 can proceed toward 1018 or optionally can terminate.

But, if no major, moderate, or minor interaction is discovered at 1012, then, at 1016, an interaction warning can be provided to the patient. The planning and/or learning module 406, 408 can direct the input/output devices 200, 302 to generate a warning and/or can schedule the warning to be provided in the plan. This warning can inform the patient that the patient may want to consult with a physician or other caregiver to ensure that there are no negative interactions between the medications. Flow of the method 1000 can proceed toward 1018 or optionally can terminate.

At 1018, a determination is made as to whether there is an interaction between any of the prescribed medications and any food or alcohol. As described above, the analysis device 132, mobile device 102, and/or wearable device 106 can store different set of interactions between prescribed medications and foods and/or between prescribed medications and alcohol (and/or other drugs). These interactions can be stored in the storage devices 404, 504, or in another location. The planning and/or learning modules 406, 408 can determine if any interactions between a prescribed medication and food or alcohol, regardless of whether the patient has indicated that the patient will be consuming the food or alcohol. If any such interaction exists, flow of the method 1000 can proceed toward 1020. If no such interaction exists, then flow of the method 1000 can proceed toward 1022.

At 1020, a determination is made as to whether the interaction between the prescribed medication and the food or alcohol is a major interaction. As described above, various interactions can be classified as major, moderate, minor, or the like. If the identified interaction between a prescribed medication and the food or alcohol is classified as a major interaction, then flow of the method 1000 can proceed toward 1006, where the plan is not created or is created without including reminders to consume the prescribed medication. If the identified interaction is not classified as a major interaction, then flow of the method 1000 can proceed toward 1023.

At 1023, an interaction warning can be provided to the patient. The planning and/or learning module 406, 408 can direct the input/output devices 200, 302 to generate a warning and/or can schedule the warning to be provided in the plan. This warning can inform the patient that the consumption of one or more than one foods and/or alcohol can interact with a prescribed medication, and/or that the patient may want to consult with a physician or other caregiver to ensure that there are no negative interactions between the medication and the food and/or alcohol.

At 1024, a determination is made as to whether the interaction between the prescribed medication and food or alcohol affects the dosage time(s) of the medication. For example, the prescription for some medications may require that the medications be taken before consuming food, the medications be taken after consuming food, or that the medications not be taken within a designated amount of time before or after eating. These requirements can restrict when the planning and/or learning modules 406, 408 can provide the reminders for consuming medications. These requirements can be obtained from the planning and/or learning modules 406, 408 examining the prescription data 126 to determine if any of these requirements apply. If the interaction does impact dosage times (and, therefore, when reminders can be given in the plan), then flow of the method 1000 can proceed toward 1026. If the interaction does not impact dosage times, then flow of the method 1000 can proceed toward 1022.

At 1026, the dosage time for the medication or medications involved in the interaction with food or alcohol is created or modified. The planning module 406 can set the reminder for consuming the medication in the plan or the learning module 408 can change a previously established reminder for consuming the medication in the plan. The reminder can be set or changed to avoid reminding the patient to consume the medication at a time that violates a requirement or prohibition on when the medication can be consumed. For example, if the prescription requires that the medication be consumed before a meal, then the module 406 and/or 408 can create or modify the plan to set the reminder before the patient normally eats a meal (e.g., based on sensor data and/or patient input). Flow of the method 1000 can then proceed toward 1022.

At 1022, a determination is made as to whether there is an interaction between any prescribed medication and a disease, such as a chronic state. In one embodiment, the planning and/or learning modules 406, 408 examine the negative interactions between the medications prescribed to the patient and any or all potential diseases that the patient may or may not have. For example, the planning module 406 and/or learning module 408 can determine if a prescribed medication has an interaction with any disease. If so, flow of the method 1000 can proceed toward 1030. Otherwise, if no prescribed medication has a negative interaction with any disease, then flow of the method 1000 can proceed toward 1028.

At 1032, a determination is made as to whether there is an interaction between a known disease of the patient and a prescribed medication. For example, the planning and/or learning modules 406, 408 can examine the medications to the patient and the member data 120 to determine if the member data 120 indicates that the patient has a disease having an interaction with a prescribed medication. The disease(s) of the patient can be stored in the member data 120 and/or can be determined by the planning and/or learning modules 406, 408 asking the patient via the input/output devices 200, 302 whether the patient has any diseases. The determined or identified diseases can be compared to the diseases having known interactions with prescription medications that are determined from the prescription data 126. If any interaction between a disease of the patient and a prescribed medication is identified, then flow of the method 1000 can proceed toward 1010, where the severity of the interaction can be determined, as described above. If no such interaction is identified, then flow of the method 1000 can proceed toward 1032.

At 1032, a list (or other presentation) of designated diseases is presented to the patient. The planning and/or learning modules 406, 408 can direct the input/output devices 200, 302 to present a list of diseases having known interactions that are classified as major (or, optionally major or moderate), as described above. The patient can select one or more of these diseases using the input/output devices 200, 302, or can provide input indicating that the patient does not have any of these diseases. Responsive to the patient indicating that the patient has at least one of the diseases (e.g., at 1034), flow of the method 1000 can proceed toward 1006, where the plan is not created or is created without including reminders to consume the prescribed medication and/or the over-the-counter medication (as described above). Responsive to the patient indicating that the patient does not have any of the listed diseases (e.g., at 1034), flow of the method 1000 can proceed toward 1028.

At 1028, the plan is created or modified. The plan can be created or modified to generate reminders to the patient to consume medications at various times that coincide with activities of the patient, as well as avoid dangerous or otherwise negative interactions. The planning module 406 and/or learning module 408 can create the plan as otherwise described herein.

The learning module 408 may modify the preliminary or initial adherence plan into a behavior-based adherence plan, and then implement the behavior-based adherence plan. This implementation may involve the processors of the mobile device 102 directing the output device 302 of the wearable device 106 and/or the output device 200 of the mobile device 102 when to provide the notifications 204 and which notifications 204 to provide.

Over time, the behaviors or behavioral patterns of the user may change, the prescriptions of the user may change (e.g., may expire and/or new prescriptions may issue), additional sensors 104, 108 may be available, etc. The learning module 408 can monitor changes in the behavioral data, changes in the pharmaceutical data, and/or additional data from the new sensors 104, 108 and modify the currently implemented adherence plan into an updated adherence plan. For example, the sensor data can indicate that the user is waking up earlier or going to sleep later, the pharmaceutical data may indicate a new prescription for the user, or the like. The learning module 408 can modify the adherence plan to account for these changes, similar to how the plan was initially created but with the new or updated information. The learning module 408 can repeatedly update the adherence plan so that the adherence plan changes as the behaviors and/or prescriptions of the user change.

In one embodiment, the learning module 408 refers to information provided by one or more than one extendable external data sources to modify or otherwise update the adherence plan. The external data sources can include data sources that provide information relevant to the adherence plan or behavior of the user subsequent to generation of the preliminary or initial adherence plan (and/or modification of this plan into the behavior-based adherence plan). Data from these sources can be used modify the adherence plan one or more than one time. As one example, an external data source can include best practice therapeutic recommendations provided by the pharmacy benefit manager device 116. A best practice recommendation may be a method or technique that has been generally accepted as superior to alternatives because the best practice recommendation produces results that are superior to those achieved by other means or because the recommendation has become a standard way (e.g., industry standard way) of doing things. A best practice recommendation may be determined from one or more than one clinical trial that examined the consumption of one or more medications.

For example, a best practice recommendation may be generated by the pharmacy benefit manager device 116 that suggests consuming the antibiotic medication with solid food. The learning module 408 can modify the adherence plan so that the notifications 204 for reminding the user to consume the antibiotic medication occur at times and/or locations where the user normally consumes meals (as determined based on the behavioral data).

As another example, a best practice recommendation may suggest consuming the statin medication at bedtime. The learning module 408 can modify the adherence plan so that the notifications 204 for reminding the user to consume the statin medication at a time that the user normally goes to sleep (as determined based on the behavioral data).

In another example, a best practice recommendation may be generated by the pharmacy benefit manager device 116 that suggests consuming the insulin with food. The learning module 408 can modify the adherence plan so that the notifications 204 for reminding the user to consume the insulin occur at times and/or locations where the user normally consumes meals (as determined based on the behavioral data).

Another external data source can include new or updated therapies provided by the pharmacy benefit manager device 116. A therapy can include a combination of prescribed medications, exercises, or behaviors. For example, certain calisthenics may be recommended for users that are of a certain age and/or consuming certain medications (e.g., medication for arthritis). The learning module 408 may update the adherence plan to include reminders for the actions and/or medications included in the therapies that are applicable to the user.

In some embodiments, the planning module 406 may create a preliminary or initial adherence plan and/or the learning module 408 may modify an adherence plan based on previous data obtained or generated by the extendable device data sources. This previous data may be data obtained by or generated by the sensors 104, 108 prior to the user first creating any adherence plan. For example, a user may wear the wearable device 106 with the sensors 104 of the wearable device 106 obtaining or generating behavioral data for other uses, such as tracking exercise regimens (e.g., training applications for a five-kilometer race), weight management applications (e.g., for monitoring caloric consumption and/or calories burned), monitoring sleep cycles, or the like. In some embodiments, the external sensor 108 and/or sensors 104 of the mobile device 102 may obtain at least some of this data.

The sensors 104, 108 of the devices 102, 106 may obtain or generate this data over an extended period of time prior to the user ever first creating an adherence plan. The planning module 406 may then take at least some of this previously obtained or generated data to create the preliminary or initial adherence plan. For example, the planning module 406 may examine the behavioral data indicative of movements of the user prior to creating the preliminary or initial adherence plan to determine when the user is typically active or awake. The planning module 406 may create the preliminary or initial adherence plan to prevent notifications 204 from being provided during inconvenient time periods based on the previously generated behavioral data, such as when the user is asleep or active. This may reduce the amount and/or extent of changes to the preliminary or initial adherence plan that the learning module 408 needs to make.

In some embodiments, a preliminary or initial adherence plan may not be created based on the previously obtained or generated behavioral data, and the learning module 408 then take at least some of this previously obtained or generated data to modify the preliminary or initial adherence plan. For example, the learning module 408 may examine the behavioral data indicative of movements of the user prior to at time at which the planning module 406 created the preliminary or initial adherence plan. The learning module 408 may modify the preliminary or initial adherence plan based on this previous behavioral data to prevent notifications 204 from being provided during inconvenient time periods based on the previously generated behavioral data.

Even though the previously generated behavioral data previously was used for other purposes, this data can provide valuable insight into the typical daily life of a user. The planning and/or learning modules 406, 408 can use this data to more efficiently create a better adherence plan that more closely abides by the typical schedule of a user, instead of generating an adherence plan that requires significant modification based on behavior data obtained only after the adherence plan is generated.

In one embodiment, an external data source can be the user. The user can provide feedback to the acquisition module of the analysis device 132 using the wearable device 106 and/or the mobile device 102. The feedback from the user can be referred to as mood feedback, and can indicate how the user is feeling at various times. As shown in FIG. 5, the wearable device 106 and/or mobile device 102 may include a query module 502 that communicates signals to the input/output device 302 to instruct the input/output device 302 to present a notification 204 requesting mood feedback from the user. In one embodiment, the adherence plan (preliminary or modified) can include notifications 204 that request mood feedback from the user.

These notifications 204 can ask the user questions about the user, such as "how are you feeling?", "are you tired?", "are you hungry?", and the like. The notifications 204 can provide selectable icons or images that indicate different answers to the question. For example, in response to the question "how are you feeling?", the input/output device 302 of the wearable device 106 and/or the mobile device 102 may display different answers, such as "good," "bad," "sick to my stomach," etc., or may provide a range of numbers, different smiley faces, etc. In response to receiving the answer from the user, the query module 502 may communicate a signal indicative of the answer to the learning module 408 of the analysis device 132, and the learning module 408 may modify the adherence plan.

In one embodiment, the learning module 408 can receive input from the user (e.g., feedback) that indicates whether the user has taken the medication or supplement, or performed the action, recommended by a notification 204. For example, responsive to receiving a notification 204 instructing the user to measure his or her blood pressure and/or take a dosage of medication, the user may test his or her blood pressure and/or consume the dosage of medication. The blood pressure sensor (e.g., a sensor 108) may communicate completion of this task to the learning module 408 (via a wireless signal) and/or the user may provide input to the mobile device 102 and/or wearable device 106 to indicate completion of the blood pressure measurement and/or consumption of the medication.

Responsive to the user providing feedback indicating that the user is not feeling well, the learning module 408 may modify the adherence plan by changing a time at which one or more than one notification 204 is provided. For example, if a user indicates that he or she is repeatedly not feeling well after consuming two different medications according to the notifications 204 provided according to the adherence plan, the learning module 408 can change the time, location, etc., at which at least one of the notifications 204 is provided. This can cause the user to consume the different medications at times that are farther apart due to the consumption of the medications according to the current plan making the user not feel well. Additional feedback can be obtained from the user over time, and the learning module 408 can further revise the adherence plan based on the additional feedback. For example, if the feedback from the user after modifying the plan indicates that the user is feeling well, then the learning module 408 can confirm that the changes to the plan are to remain in the plan. But, if the feedback from the user after modifying the plan indicates that the user continues to not feel well, then the learning module 408 may further revise the plan and/or send a signal to a healthcare provider of the user to notify the provider of the current plan and that the user is not feeling well by following the plan.

The learning module 408 in some embodiments may modify the adherence plan based on user feedback by adding one or more than one notification 204 to the plan. For example, if a user indicates that he or she is not feeling well after consuming a medication according to the currently implemented adherence plan, the learning module 408 can add a notification 204 to the plan that asks the user how he or she is feeling a designated period of time after a previous notification 204 instructs the user to consume a medication and/or after the user confirms consumption of the medication. The learning module 408 can add notifications 204 that seek feedback from the user to further tailor and personalize the adherence plan to the user.

Other user feedback may be used to confirm or change various aspects of an adherence plan. The preliminary or modified adherence plan may be presented to the user (e.g., on the input/output device 302 of the wearable device 106 and/or mobile device 102) and the user may confirm or change one or more than one of the notifications 204 in the plan. For example, the user may not wish to receive a notification 204 during a certain time period, may not want to take certain medications at certain times, or otherwise change the plan. Alternatively, the user may review the plan and not want to change the plan. The user can confirm the plan, or change and then confirm the plan, by providing user input into the mobile device 102 and/or the wearable device 106. This input may be communicated to the analysis device 132 via the network 110.

The learning module 408 can repeatedly or continually revise the adherence plan as additional sensor data, user feedback, or other information from external data sources is obtained. The learning module 408 can use incoming or new information from the sensors 104, 108, external data sources, or the like, over time to develop an adherence plan that is customized (e.g., personalized) for each user.

The planning module 406 and/or the learning module 408 can generate or modify an adherence plan based on different priorities or weights assigned to different data sets. Certain types of data or inputs into the planning module 406 and/or the learning module 408 can have greater priority in determining when and which notifications 204 are to be included in the plan than other types of data or inputs.

For example, the system 100 may give greater weight or higher priority to periods in which a user exercises than the times at which one or more than one prescribed medication is consumed. If a prescription or preliminary adherence plan dictates that a medication be taken at a time that the user normally is active (e.g., exercising), the learning module 408 may modify the adherence plan to avoid generating a notification 204 to take the medication during the active time period. This notification 204 may be modified or provided even though the time at which the notification 204 is provided may violate or not comply exactly with the prescription instructions. Instead, the notification 204 may cause the user to take the medication a little later than prescribed so as not to interfere with the exercise plan of the user.

The learning module 408 can track responses of the user to the notifications 204, such as by monitoring how often the user and/or sensors 104, 108 indicate that the user has performed a task identified by a notification 204. The learning module 408 generates a compliance score or index that represents how closely the user is abiding by the recommendations provided by the adherence plan via the notifications 204. For example, if the user consumes medications recommended by notifications 204 and/or performs other tasks recommended by notifications in response to 90% of the notifications 204, then the learning module 408 may calculate a compliance score or index of 90%. If the user consumes medications recommended by notifications 204 and/or performs other tasks recommended by notifications in response to 30% of the notifications 204, however, then the learning module 408 may calculate a compliance score or index of only 30%.

Depending on performance of the user according to the adherence plan, the learning module 408 may direct the input/output device 302 of the mobile device 102 and/or wearable device 106 to communicate a signal to an external entity, such as a healthcare provider of the user. For example, responsive to the compliance score or index of the user falling below a designated threshold (which may be established or set by the provider), the learning module 408 may instruct the device 200 to send a notice to the provider informing the provider of the user not following or being able to follow the adherence plan. The provider may be prompted by this signal to contact the user and change prescribed medications or other factors in an effort to increase compliance with the adherence plan.

Optionally, the modules that receive user input, obtain the pharmaceutical data, generate adherence plans, and/or modify adherence plans may be in the mobile device 102 and/or wearable device 106. For example, one or more of the modules 400, 402, 406, 408 described herein may be included in the mobile device 102 and/or wearable device 106.

In one embodiment, the analysis device 132 can receive data from the mobile device 102 and/or wearable device 106 via the network 110. This data can represent or indicate details of the adherence plan, compliance scores, or the like, from the mobile devices 102 and/or wearable devices 106 of multiple users. In some embodiments, the data can include demographic data, such as ages, genders, ethnicities, medical conditions or ailments, or the like, of the users.

The analysis device 132 can examine the compliance scores of multiple different users following multiple, different (or at least partially identical) adherence plans to determine whether any of the adherence plans should be recommended for these or other users. This examination can include the processors of the analysis device 132 identifying adherence plans of users associated with relatively good or high (e.g., at least 90%) compliance scores. These compliance scores can indicate that the adherence plans for these users work well to keep or entice the users to take the prescribed medications, activities, supplements, etc., according to the adherence plans of the respective users.

In one embodiment, the analysis device 132 can recommend an adherence plan or a combined adherence plan (e.g., an adherence plan combined from two or more other adherence plans) to a user as an adherence plan. The analysis device 132 can determine demographic information of the user (e.g., the age, gender, ethnicity, location, etc.) and the data provided by the extendable internal data sources for the user (e.g., the prescribed medications, dosages, and dosing frequency). This information and data can be compared to demographic information and the data from the extendable internal data sources of other users associated with other adherence plans (having high or large compliance scores). If the user has the same or similar demographic information and data from the internal data sources, then the analysis device 132 may communicate a signal to the mobile device 102 via the network 110 to recommend at least one of the adherence plans. For example, the mobile device 102 of a user being in the same demographic group (e.g., the same age group, same gender, same ethnicity, etc.) and having one or more of the same prescriptions may be provided with the adherence plan (or a portion thereof) of another user or users having high compliance scores.

The analysis device 132 can generate and send signals to healthcare providers based on the compliance scores associated with different adherence plans. These signals can warn the providers of low compliance scores associated with adherence plans having notifications 204 for the same medications and, optionally, for the same demographic groups of users. For example, if the analysis device 132 determines that there are low compliance scores (e.g., 30% or less) for users taking the same prescribed medications or combination of prescribed medications and having the same or similar age (e.g., within five years of each other), same gender, and/or same ethnicity, then the analysis device 132 may communicate a signal to one or more healthcare providers to warn the providers that the users in this demographic group are struggling to comply with the instructions for consuming the prescribed medications. As another example, if the analysis device 132 determines that there are high compliance scores (e.g., 90% or more) for users taking the same prescribed medications or combination of prescribed medications and having the same or similar age (e.g., within five years of each other), same gender, and/or same ethnicity, then the analysis device 132 may communicate a signal to one or more healthcare providers to notify the providers that the users in this demographic group are successfully complying with the instructions for consuming the prescribed medications.

The analysis device 132 can generate a summary, or dashboard, of analytics for the user to review and obtain information into the behaviors and/or goals of the user. This summary can be communicated to the mobile device 102 via the network 110 for presentation on the mobile device 102. The summary can include compliance scores for the entire adherence plan, for part of the adherence plan (e.g., for one or more than one particular medication), for certain time periods (e.g., certain weeks, days, months, etc.), or the like. The summary also can point out changes in the compliance scores that occur responsive to changes in the behavioral data of the user. For example, the summary can point out where the compliance score increased or decreased for a user responsive to the user beginning or stopping an exercise program, taking one or more than one additional medication or supplement, etc.

Figure 8:
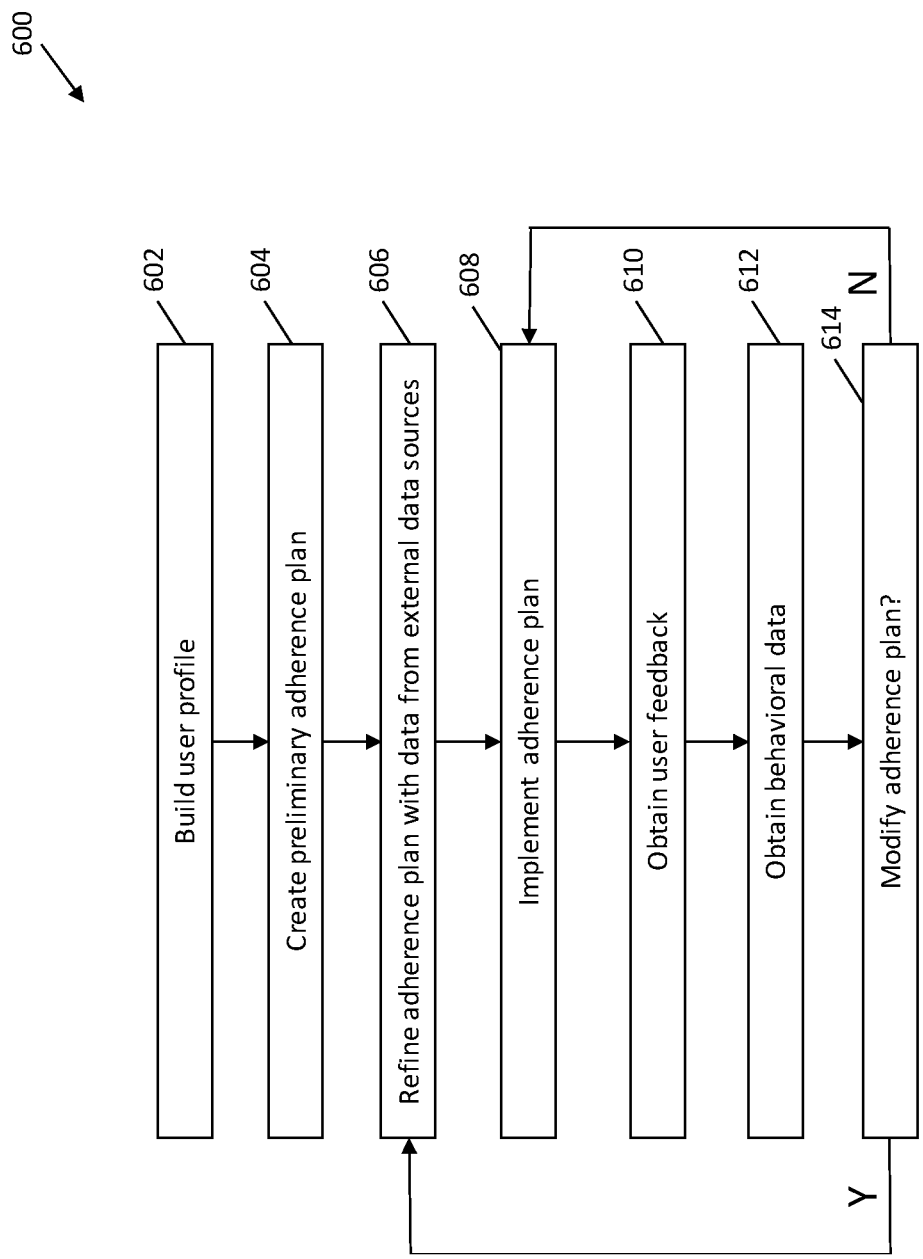
FIG. 8 is an example process flow illustrating a method for generating and personalizing reminders to increase medical therapy adherence.

FIG. 8 is an example process flow illustrating a method 600 for generating and personalizing reminders to increase medical therapy adherence. The method 600 may be used to create and/or modify the adherence plans described herein in order to provide and customize the notifications 204 provided to users to increase how closely the users follow the prescribed instructions for consuming medications.

At block 602, a user profile is built. This can involve obtaining information about a user, determining if the user currently has pharmaceutical data stored with the pharmacy benefit manager device 116, and obtaining at least part of this pharmaceutical data, as described above. If the user does not have pharmaceutical data stored with the pharmacy benefit manager device 116, or has additional pharmaceutical data stored elsewhere, then the user may provide this information for inclusion in the profile of the user, such as by taking images of medication containers (also as described above).

At block 604, a preliminary adherence plan is generated. As described above, this plan may be based on the pharmaceutical data of the user and optionally on previously obtained behavioral data. The preliminary adherence plan may need to be modified over time, however, based on new and/or additional data provided by sensors, the user, or other sources.

At block 606, the adherence plan may be refined with data from one or more than one external data source. For example, sensors 104, 108 can provide measurements or other sensed characteristics of the user or activity level of the user, the user may provide input, best practices may be determined, or other data can be obtained. This information can be used to modify the adherence plan, such as by ensuring that reminders 204 are not provided during inconvenient time periods for the user, that reminders 204 do not conflict or result in conflict with a best practice recommendation, or the like.

At block 608, the adherence plan is implemented. The adherence plan may be implemented by directing the wearable device 106 (or, optionally, the mobile device 102) to present the notifications 204 designated by the adherence plan to the user at the times designated by the adherence plan, as described above.

At block 610, user feedback is obtained. This feedback can be input from the user that responds to queries from the wearable device 106 and/or mobile device 102. For example, the feedback can include responses to questions presented to the user, such as "how are you feeling?".

At block 612, behavioral data is obtained. This data can be provided by the sensors 104, 108 and/or the user, and can represent how the user behaves on a regular basis. For example, this behavioral data can indicate when the user is normally home, when the user is active or exercising, when the user is sleeping, etc., as described above.

At decision point 614, a determination is made as to whether the adherence plan should be modified. For example, the user feedback, behavioral data, and/or any new or additional data from external and/or internal data sources may be examined to determine if the adherence plan being currently implemented should be modified. The currently implemented adherence plan may need to be modified responsive to one or more than one current prescription of the user expiring, one or more than one new prescription for the user, the behavioral data indicating that the notifications 204 are being provided to the user at times or locations that are inconvenient for the user to take the medication, the compliance score indicating that the user is not following the adherence plan, the user feedback indicating that the adherence plan is not making the user feel well or better, etc.

Responsive to determining that the adherence plan is to be changed at block 614, flow of the method 600 may return toward block 606. This results in the adherence plan being refined (e.g., modified) based on the user input, behavioral data, and/or other data. The method 600 may proceed in a loop one or more additional times to repeatedly refine the adherence plan.

Responsive to determining that the adherence plan is not to be changed at block 614, flow of the method 600 may return toward block 608. This results in the adherence plan not being refined, but the user feedback, behavioral data, etc., continuing to be monitored for potential further revisions of the adherence plan.

Figure 9:
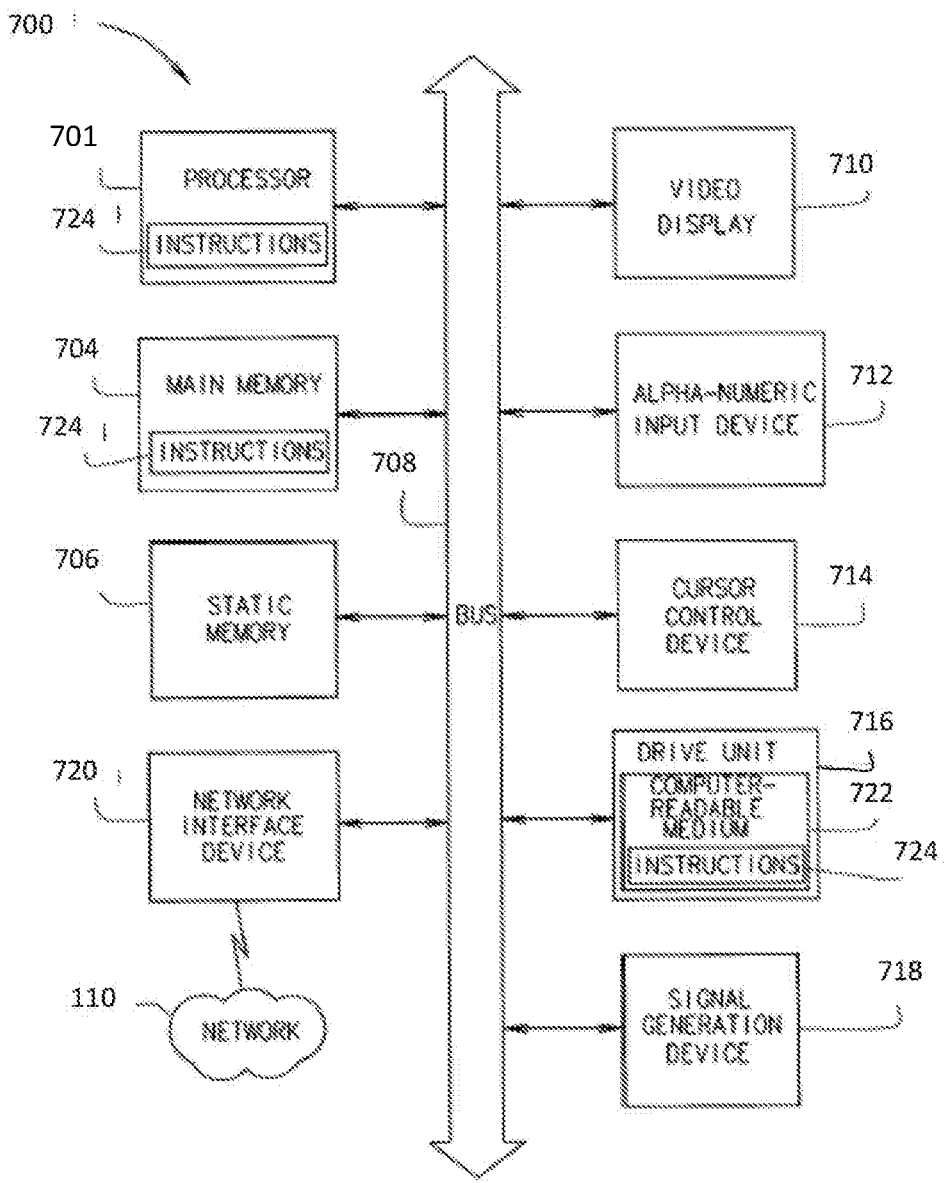
FIG. 9 shows a block diagram a computer system within which sets of instructions may be executed causing the machines to perform any one or more than one methods, processes, operations, or methodologies discussed herein.

FIG. 9 shows a block diagram of the analysis device 132, the mobile device 102, and the wearable device 106 in the example form of a computer system 700 within which a set of instructions may be executed causing the machine to perform any one or more than one methods, processes, operations, or methodologies discussed herein. The analysis device 132, for example, may include the functionality of the one or more than one computer system 700. The mobile device 102, for example, may include the functionality of the one or more than one computer system 700. The wearable device 106, for example, may include the functionality of the one or more than one computer system 700. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 700 includes one or more processors 701 (e.g., a central processing unit (CPU), a graphics processing unit (GPU) or both, etc.), a main memory 704 and a static memory 706, which communicate with each other via a bus 708. The computer system 700 further includes a video display unit 710 (e.g., a liquid crystal display (LCD) or a cathode ray tube (CRT), etc.). The computer system 700 also includes an alphanumeric input device 712 (e.g., a physical or displayed keyboard, etc.), a cursor control device 714 (e.g., a mouse, etc.), a drive unit 716, a signal generation device 718 (e.g., a speaker, etc.) and a network interface device 720.

The drive unit 716 includes a computer readable medium 722 (CPU Readable Medium in FIG. 9) on which is stored one or more than one sets of instructions 724 (e.g., software, etc.) embodying any one or more than one methodologies or functions described herein. The instructions 724 may also reside, completely or at least partially, within the main memory 704 and/or within the processor 701 during execution thereof by the computer system 700, the main memory 704 and the processor 701 also constituting non-transitory computer readable media. When loaded with the instructions 724, the processor 701 is a machine dedicated to only the present processes and methodologies.

The instructions 724 may further be transmitted or received over the network 110 via the network interface device 720.

While the computer-readable medium 722 is shown in an example embodiment to be a single medium, the term "computer-readable medium" should be taken to include a single medium or multiple media (e.g., a centralized or distributed database, and/or associated caches and servers, etc.) that store the one or more than one sets of instructions. The term "computer-readable medium" shall also be taken to include any medium that can store or encoding a set of instructions for execution by the machine and that cause the machine to perform any one or more than one methodologies of the present invention. The term "computer-readable medium" shall accordingly be taken to include, but not be limited to, solid-state memories, and optical media, and magnetic media. In some embodiments, the computer-readable medium is a non-transitory computer-readable medium. In other examples, a computer-readable medium is any medium that satisfies statutory requirements and stores instructions for use by a machine.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The term "based on" or using, as used herein, reflects an open-ended term that can reflect other elements beyond those explicitly recited.

Certain systems, apparatus, applications or processes are described herein as including several modules. A module may be a unit of distinct functionality that may be presented in software, hardware, or combinations thereof. When the functionality of a module is performed in any part through software, the module includes a computer-readable medium. The modules may be regarded as being communicatively coupled.

The embodiments of the present disclosure generally provide for a plurality of circuits or other electrical devices, which can be used in units, modules, systems, and subsystems and the like. All references to such and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical/operational implementation that is desired. It is recognized that any circuit or other electrical device disclosed herein may include any number of microprocessors, discrete circuit components, integrated circuits, memory devices (e.g., FLASH, random access memory (RAM), read only memory (ROM), electrically programmable read only memory (EPROM), electrically erasable programmable read only memory (EEPROM), or other suitable variants thereof, etc.) and instructions (e.g., software, etc.) which co-act with one another to perform operation(s) disclosed herein. In addition, any one or more than one electric devices may be configured to execute a computer-program that is embodied in a computer readable medium that is programmed to perform any number of the functions and features as disclosed. The computer readable medium may be non-transitory or in any form readable by a machine or electrical component.

The inventive subject matter may be represented in a variety of different embodiments of which there are many possible permutations.

In an example embodiment, a system includes one or more processors of a mobile device. The one or more processors are configured to obtain pharmaceutical data of a user from a pharmacy benefit manager. The pharmaceutical data includes prescription data indicative of at least one medication prescribed for the user. The pharmaceutical data is used by the pharmacy benefit manager to adjudicate a claim by the user for a pharmaceutical benefit. The one or more processors also are configured to determine an adherence plan for reminding the user to consume the at least one medication. The adherence plan determined based on the pharmaceutical data obtained from the pharmacy benefit manager. The one or more processors also are configured to generate one or more notifications on one or more of a wearable device or an output device of the mobile device at one or more times that are based on the adherence plan. The one or more notifications instructing the user when to consume the at least one medication.

In another example embodiment, a method includes obtaining pharmaceutical data of a user from a pharmacy benefit manager. The pharmaceutical data includes prescription data indicative of at least one medication prescribed for the user. The pharmaceutical data is used by the pharmacy benefit manager to adjudicate a claim by the user for a pharmaceutical benefit. The method also includes determining an adherence plan for reminding the user to consume the at least one medication. The adherence plan is determined based on the pharmaceutical data obtained from the pharmacy benefit manager. The method also includes generating one or more notifications on one or more of a wearable device or a mobile device of the user at one or more times that are based on the adherence plan. The one or more notifications instruct the user when to consume the at least one medication.

In another example embodiment, a method includes obtaining prescription data of a user at a mobile device from a pharmacy benefit manager. The prescription data is indicative of at least one medication prescribed for the user. The prescription data is used by the pharmacy benefit manager to adjudicate a claim by the user for a pharmaceutical benefit. The method also includes obtaining behavioral data of the user from at least one sensor of one or more of the mobile device or a wearable device of the user. The behavioral data is indicative of movement of the user. The method also includes determining an adherence plan for reminding the user to consume the at least one medication. The adherence plan is determined based on the prescription data obtained from the pharmacy benefit manager and the behavioral data obtained from the at least one sensor. The method also includes generating one or more notifications on one or more of the wearable device or the mobile device at one or more times that are based on the adherence plan. The one or more notifications instruct the user when to consume the at least one medication.

Thus, methods and systems for generating and personalizing reminders to increase medical therapy adherence have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks may be shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more than one steps within a method may be executed in different order (or concurrently) without altering the principles of the present disclosure. Further, although each of the embodiments is described above as having certain features, any one or more than one of those features described with respect to any embodiment of the disclosure can be implemented in and/or combined with features of any of the other embodiments, even if that combination is not explicitly described. In other words, the described embodiments are not mutually exclusive, and permutations of one or more than one embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more than one intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more than one interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuitry that, in combination with additional processor circuits, executes some or all code from one or more than one modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more than one modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more than one particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more than one operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The invention claimed is:

1. A method comprising:
receiving, by a computing system via a communication network from a pharmacy benefit manager device, a data scheduling request identifying a first designated medical consumable;
accessing, by the computing system from a computer memory, a plurality of first document types indicating frequencies for ingesting medical consumables including the first designated medical consumable;
determining whether a drug interaction occurs between the first medical consumable and a second designated medical consumable; and
based on determining whether the drug interaction occurs,
identifying a first frequency for consuming the first designated medical consumable, by the computing system, the frequencies comprising at least the first frequency;
monitoring movement of a patient, by:
receiving at least one output signal from one or more sensors of a mobile electronic device of the patient, by the computing system; and
creating a pattern of personal activity behavior of the patient based on the at least one output signal;
identifying one or more temporal opportunity windows, by:
determining active periods of time and inactive periods of time, based on the pattern of personal activity behavior; and
identifying time periods outside of the inactive periods and the active periods, the time periods indicating when one or more of the medical consumables are to be ingested by the patient, and the one or more temporal opportunity windows comprising the time periods;
determining, by the computing system, one or more matches between the first frequency and the one or more temporal opportunity windows;
creating an adherence schedule based on the one or more matches, by the computing system, the adherence schedule for generating and presenting reminders to ingest the first designated medical consumable, via the mobile electronic device of the patient;
monitoring subsequent movement of the patient after creation of the adherence schedule, by the computing system, based on subsequent sensor output signals provided by the one or more sensors;
determining a change to the pattern of personal activity behavior based on the subsequent movement, by the computing system, the change including a modification to the one or more temporal opportunity windows based on a patient location being inside a geofenced area; and
modifying the adherence schedule based on the change, by the computing system, to create a modified adherence schedule for presenting one or more of the reminders via the mobile electronic device for the patient to consume the first designated medical consumable upon arrival inside the geofenced area.

2. The method of claim 1, wherein determining the change to the pattern of personal activity behavior includes determining one or more new matches between the first frequency and the modification to the one or more temporal opportunity windows, wherein the adherence schedule is modified according to the one or more new matches.

3. The method of claim 1, further comprising:
generating the one or more of the reminders according to the modified adherence schedule, by the computing system; and
presenting the one or more of the reminders via the mobile electronic device for the patient.

4. The method of claim 1, wherein the data scheduling request identifies the second designated medical consumable; and
wherein the method further comprises:
accessing a plurality of second document types indicating potential drug interactions for the second designated medical consumable; and
determining the drug interaction does not occur, based on the plurality of second document types.

5. The method of claim 4, further comprising:
generating the one or more of the reminders according to the adherence schedule, by the computing system; and
presenting the one or more of the reminders via the mobile electronic device for the patient.

6. The method of claim 1, wherein the data scheduling request identifies the second designated medical consumable; and
wherein the method further comprises:
accessing a plurality of second document types indicating potential drug interactions for the second designated medical consumable;
determining the drug interaction occurs, based on the plurality of second document types; and
preventing creation of the adherence schedule, based on the drug interaction.

7. The method of claim 1, wherein the data scheduling request identifies the second designated medical consumable; and wherein the method further comprises:
accessing a plurality of second document types indicating potential drug interactions for the second designated medical consumable;
determining the drug interaction occurs, based on the plurality of second document types; and
preventing generation of the one or more of the reminders at times contradictory to the drug interaction, based on the one or more temporal opportunity windows and the plurality of second document types.

8. The method of claim 1, further comprising:
accessing a plurality of third document types indicating the drug interaction between the first designated medical consumable and one or more non-medical consumables; and
preventing generation of the reminders at times contradictory to the drug interaction between the first designated medical consumable and the one or more non-medical consumables based on the one or more temporal opportunity windows and the plurality of third document types.

9. The method of claim 1, further comprising:
accessing a plurality of fourth document types indicating an interaction between the first designated medical consumable and one or more chronic states; and
identifying the one or more temporal opportunity windows based on the plurality of fourth document types.

10. A tangible and non-transitory computer readable storage medium comprising instructions that direct at least one processor to:
receive, by a computing system via a communication network from a pharmacy benefit manager device, a data scheduling request identifying a first designated medical consumable;
access, by the computing system from a computer memory, a plurality of first document types indicating frequencies for ingesting medical consumables including the first designated medical consumable;
determine whether a drug interaction occurs between the first medical consumable and a second medical consumable; and
based on determining whether the drug interaction occurs, identify a first frequency for consuming the first designated medical consumable, by the computing system, the frequencies comprising at least the first frequency;
monitor movement of a patient, by:
receiving at least one output signal from one or more sensors of a mobile electronic device of the patient, by the computer system; and
creating a pattern of personal activity behavior of the patient based on the at least one output signal;
identify one or more temporal opportunity windows, by:
determining active periods of time and inactive periods of time, based on the pattern of personal activity behavior; and
identifying time periods outside of the inactive periods and the active periods, the time periods indicating when one or more of the medical consumables are to be ingested by the patient, and the one or more temporal opportunity windows comprising the time periods;
determine, by the computing system, one or more matches between the first frequency and the one or more temporal opportunity windows;

create an adherence schedule based on the one or more matches, by the computing system, the adherence schedule for generating and presenting reminders to ingest the first designated medical consumable, via the mobile electronic device of the patient;
monitor subsequent movement of the patient after creation of the adherence schedule, by the computing system, based on subsequent sensor output signals provided by the one or more sensors;
determine a change to the pattern of personal activity behavior based on the subsequent movement, by the computing system, the change including a modification to the one or more temporal opportunity windows determined based on a patient location being inside a geofenced area; and
modify the adherence schedule based on the change, by the computing system, to create a modified adherence schedule for presenting one or more of the reminders via the mobile electronic device for the patient for the patient to consume the first designated medical consumable upon arrival inside the geofenced area.

11. The non-transitory, computer readable storage medium of claim 10, wherein the instructions further direct the at least one processor to:
determine one or more new matches between the first frequency and the modification to the one or more temporal opportunity windows; and
modify the adherence schedule according to the one or more new matches that are determined.

12. The non-transitory, computer readable storage medium of claim 10, wherein the instructions further direct the at least one processor to:
generate the one or more of the reminders according to the modified adherence schedule, by the computing system; and
present the one or more of the reminders via the mobile electronic device for the patient.

13. The non-transitory, computer readable storage medium of claim 10, wherein the data scheduling request identifies the second designated medical consumable; and
wherein the instructions further direct the at least one processor to:
access a plurality of second document types indicating potential drug interactions for the second designated medical consumable; and
determine the drug interaction does not occur, based on the plurality of second document types.

14. The non-transitory, computer readable storage medium of claim 13, wherein the instructions further direct the at least one processor to:
generate the one or more of the reminders according to the adherence schedule, by the computing system; and
present the one or more of the reminders via the mobile electronic device for the patient.

15. The non-transitory, computer readable storage medium of claim 10, wherein the data scheduling request identifies the second designated medical consumable; and
wherein the instructions further direct the at least one processor to:
access a plurality of second document types indicating potential drug interactions for the second designated medical consumable;
determine the drug interaction occurs, based on the plurality of second document types; and
prevent creation of the adherence schedule, based on the drug interaction.

16. The non-transitory, computer readable storage medium of claim 10, wherein the data scheduling request identifies the second designated medical consumable; and
wherein the instructions further direct the at least one processor to:
access a plurality of second document types indicating potential drug interactions for the second designated medical consumable;
determine the drug interaction occurs, based on the plurality of second document types; and
prevent generation of the one or more of the reminders at times contradictory to the drug interaction, based on the one or more temporal opportunity windows and the plurality of second document types.

17. The non-transitory, computer readable storage medium of claim 10, wherein the instructions also direct the at least one processor to:
access a plurality of third document types indicating the drug interaction between the first designated medical consumable and one or more non-medical consumables; and
prevent generation of the reminders at times contradictory to the drug interaction between the first designated medical consumable and the one or more non-medical consumables based on the one or more temporal opportunity windows and the plurality of third document types.

18. The non-transitory, computer readable storage medium of claim 10, wherein the instructions also direct the at least one processor to:
access a plurality of fourth document types indicating an interaction between the first designated medical consumable and one or more chronic states; and
identify the one or more temporal opportunity windows based on the plurality of fourth document types.

19. A method comprising:
receiving, by a computing system via a communication network from a pharmacy benefit manager device, a data scheduling request identifying a first designated medical consumable;
accessing, by the computing system from a computer memory, a plurality of first document types indicating frequencies for ingesting medical consumables including the first designated medical consumable;
determining whether a drug interaction occurs between the first medical consumable and a second designated medical consumable; and
based on determining the drug interaction does not occur, identifying a first frequency for consuming the first designated medical consumable, by the computing system, the frequencies comprising at least the first frequency;
monitoring movement of a patient, by:
receiving at least one output signal from one or more sensors of a mobile electronic device of the patient, by the computing system; and
creating a pattern of personal activity behavior of the patient based on the at least one output signal;
identifying one or more temporal opportunity windows, by:
determining active periods of time and inactive periods of time, based on the pattern of personal activity behavior; and
identifying time periods outside of the inactive periods and the active periods, the time periods indicating when one or more of the medical consumables are to be ingested by the patient, and the one or more temporal opportunity windows comprising the time periods;
determining, by the computing system, one or more matches between the first frequency and the one or more temporal opportunity windows;
creating an adherence schedule based on the one or more matches, by the computing system, the adherence schedule for generating and presenting reminders to ingest the first designated medical consumable, via the mobile electronic device of the patient;
monitoring subsequent movement of the patient after creation of the adherence schedule, by the computing system, based on subsequent sensor output signals provided by the one or more sensors;
determining a change to the pattern of personal activity behavior based on the subsequent movement, by the computing system, the change including a modification to the one or more temporal opportunity windows based on a patient location being inside a geofenced area; and
modifying the adherence schedule based on the change, by the computing system, to create a modified adherence schedule for presenting one or more of the reminders via the mobile electronic device for the patient to consume the first designated medical consumable upon arrival inside the geofenced area.

20. The method of claim 19, further comprising:
generating the one or more of the reminders according to the modified adherence schedule, by the computing system; and
presenting the one or more of the reminders via the mobile electronic device for the patient.

* * * * *